(12) United States Patent
Tovey et al.

US008426123B2

(10) Patent No.: US 8,426,123 B2
(45) Date of Patent: Apr. 23, 2013

(54) METHOD FOR CONDUCTING AN ASSAY FOR NEUTRALIZING ANTIBODIES

(75) Inventors: Michael G. Tovey, Paris (FR); Christophe Lallemand, Paris (FR)

(73) Assignees: Biomonitor Limited, Galway (IE); Le Centre Nationale de la Recherche Scientifique, Paris (FR)

( * ) Notice: Subject to any disclaimer, the term of this patent is extended or adjusted under 35 U.S.C. 154(b) by 120 days.

(21) Appl. No.: 12/260,871

(22) Filed: Oct. 29, 2008

(65) Prior Publication Data
US 2009/0136947 A1 May 28, 2009

Related U.S. Application Data

(60) Provisional application No. 60/983,813, filed on Oct. 30, 2007.

(51) Int. Cl.
*C12Q 1/00* (2006.01)
(52) U.S. Cl.
USPC .................................................. 435/4
(58) Field of Classification Search ........................ None
See application file for complete search history.

(56) References Cited

U.S. PATENT DOCUMENTS

| | | | |
|---|---|---|---|
| 5,401,629 | A | 3/1995 | Harpold et al. |
| 5,436,128 | A | 7/1995 | Harpold et al. |
| 5,707,803 | A | 1/1998 | Lamb et al. |
| 6,316,692 | B1 | 11/2001 | Readhead et al. |
| 7,045,281 | B2 | 5/2006 | Livelli et al. |
| 7,470,536 | B2 | 12/2008 | Tovey et al. |
| 2004/0235157 | A1 | 11/2004 | Tovey et al. |
| 2005/0042643 | A1 | 2/2005 | Cotter et al. |
| 2007/0099245 | A1 | 5/2007 | Gorovits et al. |
| 2008/0081327 | A1 | 4/2008 | Livelli et al. |
| 2008/0138818 | A1 | 6/2008 | Tovey et al. |
| 2008/0248516 | A1 | 10/2008 | Livelli et al. |
| 2009/0111178 | A1 | 4/2009 | Tovey et al. |
| 2009/0136947 | A1 | 5/2009 | Tovey et al. |

FOREIGN PATENT DOCUMENTS

| | | | |
|---|---|---|---|
| WO | 2004027374 | A2 | 4/2004 |
| WO | 2004039990 | A2 | 5/2004 |
| WO | WO 2004/039990 | A2 * | 5/2004 |
| WO | 2008055153 | A2 | 5/2008 |

OTHER PUBLICATIONS

Malucchi et al (Neurology, Jun. 2004, 62(11):2031-2037).*
Lallemand et al (Journal of Leukocyte Biology, 1996, 60: 137-146).*
Office Action dated Apr. 7, 2006 of U.S. Appl. No. 10/677,777.
Office Action dated Sep. 7, 2007 of U.S. Appl. No. 10/677,777.
Office Action dated Mar. 19, 2008 of U.S. Appl. No. 10/677,777.
Office Action dated Oct. 16, 2009 of U.S. Appl. No. 11/765,262.
Office Action dated May 21, 2010 of U.S. Appl. No. 11/765,262.
Office Action dated Mar. 17, 2011 of U.S. Appl. No. 11/765,262.
Office Action dated Sep. 2, 2010 of U.S. Appl. No. 11/328,965.
Office Action dated Apr. 14, 2010 of U.S. Appl. No. 12/336,121.
Final Office Action dated Nov. 24, 2010 of U.S. Appl. No. 12/336,121.
Ausubel et al, Current protocols in molecular biology, 4:A.3F.5-10.
ATCC catalog 1998.
Aschele et al., Cancer Research, 52:1855-1864 (1992).
Darnay et al., Activation of NF-kB by RANK requires tumor necrosis factor receptor-associated factor (TRAF) 6 and NF-kB-inudcing kinase, The Journal of Biological Chemistry, 274(12):7724-7731 (1999).
Deisenhammer F, Schellekens H, Bertolotto A., Measurement of neutralizing antibodies to interferon beta in patients with multiple sclerosis, J. Neurol. (2004) 251(Suppl. 2):11:31-11:39.
Ganster et al., Complex regulation of human inducible nitric oxide synthase gene transcription by Stat 1 and NF-kB, PNAS, 98(15):8638-8643 (2001).
Farrell et al., Development and validation of luciferase reporter gene assay to measure anti-interferon beta neutralizing antibodies, Neurology, 68(12):(Suppl. 1):A117-A118 (2007).
Lleonart et al., "A novel, quantitative bioassay for type I interferon using a recombinant indicator cell line" Biotechnology 8:1263-1267(1990).
Manna et al., IFN-alpha suppresses activation of nuclear transcription factors NF-kappa B and activator protein 1 and potentiates TNF-induced apoptosis, Journal of Immunology, 165(9)4927-4934 (2000).
Shen et al., The Journal of Biological Chemistry, 261(17):7762-7770 (1986).
Tovey et al., Characterization of neutralizing antibodies to interferons using a novel cell-based assay, Journal of Interferon and Cytokine Research, 27(8):735 (2007).
Bertolotto et al., Interferon beta neutralizing antibodies in multiple sclerosis: neutralizing activity and cross-reactivity with three different preparations, Immunopharmacology, 48:95-100 (2000).

(Continued)

Primary Examiner — Sean Aeder
(74) Attorney, Agent, or Firm — Browdy and Neimark, PLLC

(57) ABSTRACT

A method for conducting a neutralization assay for the determination of the titer of antibodies in a sample is provided which is an improvement over existing neutralization assays because the sensitivity of the reporter gene assay to determine neutralization is increased by the use of a "one time use" cell line transformed with a reporter gene construct. The titer is determined for antibodies specific for a predetermined target molecule that activates the signal transduction activity of a cell surface protein or a pattern recognition receptor or are specific for an antagonist for the predetermined target molecule.

25 Claims, 13 Drawing Sheets

OTHER PUBLICATIONS

Nagy et al., Preparing feeder cell layers from STO or mouse embryo fibroblast (MEF) cells: Treatment with γ-irradiation, Cold Spring Harb. Protoc.; 2006; doi:10.1101/pdb.prot4400.

Nagy et al., Preparing feeder cell layers from STO or mouse embryo fibroblast (MEF) cells: Treatment with mitomycin C, Cold Spring Harb. Protoc.; 2006; doi:10.1101/pdb.prot4399.

Huntsman et al., Blood Groups and Enzymes of Human Red Cells after Five Years' Storage in Liquid Nitrogen. British Medical Journal, vol. 4, 25 pp. 458-460 (1967).

Kushnaryov et al., "Ultrastructural Localization of Interferon Receptors on the Surfaces of Cultured Cells and Erythrocytes" Infection and Immunity, vol. 36, No. 2, p. 811-821 (1982).

Hodgins et al. Preservation of Trout and Salmon Erythrocytes for Blood Typing by Freezing with Dimethyl Sulphoxide. Nature, vol. 201, 28, pp. 1336-1337 (1964).

Yang et al., PNAS, 87:9568-9572 (1990).

Berry et al., Biochemical Pharmacology, 62:582-591 (2001).

Wei et al., Sheng Wu Hua Xue Yu Sheng Wu Wu Li Lue Bao, Shanghai, 33(1):123-127, abstract (2001).

Eichbaum et al., J. Exp. Med., 179:1985-1996 (1994).

Kim et al., Immunopharmacology and Immunotoxicology, 23(1):55-66 (2001).

Grossberg, et al., "The Expression of Potency of Neutralizing Antibodies for Interferons and Other Cytokines, Biotherapy" 10:93-98 (1997).

Grossberg et al., "The neutralization of interferons by antibody. I. Quantitative and theoretical analyses of the neutralization reaction in different bioassay systems" J Interferon Cytokine Res 21:729-42 (2001a).

Grossberg, et al. "The neutralization of interferons by antibody. II. Neutralizing antibody unitage and its relationship to bioassay sensitivity: the tenfold reduction unit" J Interferon Cytokine Res 21:743-55. (2001b).

Grossberg et al. "The Neutralization of Interferons by Antibody III. The Constant Antibody Bioassay, A Highly Sensitive Quantitative Detector of Low Antibody Levels" J Interferon Cytokine Res 29:93-104 (2009).

Lallemand et al., Constitutive expression of specific interferon isotypes in peripheral blood leukocytes from normal individuals and in promonocytic U937 cells, Journal of Leukocyte Biology, 60:137-146 (1996).

Canosi et al., A highly precise reporter gene bioassay for type I interferon, Journal of Immunological Methods, 199:69-76 (1996).

Files et al., A novel sensitive and selective bioassay for human type I interferons, Journal of Interferon and Cytokine Research, 18:1019-1024 (1998).

Lewis, A sensitive biological assay for interferons, Journal of Immunological Methods, 185:9-17 (1995).

Button et al., Aequorin-expressing mammalian cell lines used to report Ca2+ mobilization, Cell Calcium (Oct. 1993) 14(9):663-671.

Ahern H., Biochemical, reagents kits offer scientists good return on investment, The Scientist, 9(15):20-27 (1995).

Office Action dated Nov. 24, 2010 of U.S. Appl. No. 12/336,121.

Office Action dated Jun. 7, 2011 of U.S. Appl. No. 11/928,965.

* cited by examiner

SEQUENCE LISTING

```
<160> NUMBER OF SEQ ID NOS: 8

<210> SEQ ID NO 1
<211> LENGTH: 5849
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (328)..(1980)

<400> SEQUENCE: 1
cccgggaggt accgagctct tacgcgtgct agctcgactc gggaaaggga aaccgaaact         60 gaagccctc  gggaaaggga aaccgaaact gaagcccgat ctgcatctca attagtcagc        120
aaccatagtc ccgcccctaa ctccgcccat cccgcccta  actccgccca gttccgccca        180
ttctccgccc catggctgac taattttttt tatttatgca gaggccgagg ccgcctcggc        240
ctctgagcta ttccagaagt agtgaggagg cttttttgga ggcctaggct tttgcaaaaa        300
gcttggcatt ccggtactgt tggtaaa atg gaa gac gcc aaa aac ata aag aaa        354
                                Met Glu Asp Ala Lys Asn Ile Lys Lys
                                  1               5 ggc ccg gcg cca ttc tat cct cta gag gat gga acc gct gga gag caa         402
Gly Pro Ala Pro Phe Tyr Pro Leu Glu Asp Gly Thr Ala Gly Glu Gln
 10              15                  20                  25 ctg cat aag gct atg aag aga tac gcc ctg gtt cct gga aca att gct         450
Leu His Lys Ala Met Lys Arg Tyr Ala Leu Val Pro Gly Thr Ile Ala
                 30                  35                  40 ttt aca gat gca cat atc gag gtg aac atc acg tac gcg gaa tac ttc         498
Phe Thr Asp Ala His Ile Glu Val Asn Ile Thr Tyr Ala Glu Tyr Phe
             45                  50                  55 gaa atg tcc gtt cgg ttg gca gaa gct atg aaa cga tat ggg ctg aat         546
Glu Met Ser Val Arg Leu Ala Glu Ala Met Lys Arg Tyr Gly Leu Asn
         60                  65                  70 aca aat cac aga atc gtc gta tgc agt gaa aac tct ctt caa ttc ttt         594
Thr Asn His Arg Ile Val Val Cys Ser Glu Asn Ser Leu Gln Phe Phe
     75                  80                  85 atg ccg gtg ttg ggc gcg tta ttt atc gga gtt gca gtt gcg ccc gcg         642
Met Pro Val Leu Gly Ala Leu Phe Ile Gly Val Ala Val Ala Pro Ala
 90                  95                 100                 105 aac gac att tat aat gaa cgt gaa ttg ctc aac agt atg aac att tcg         690
Asn Asp Ile Tyr Asn Glu Arg Glu Leu Leu Asn Ser Met Asn Ile Ser
                110                 115                 120 cag cct acc gta gtg ttt gtt tcc aaa aag ggg ttg caa aaa att ttg         738
Gln Pro Thr Val Val Phe Val Ser Lys Lys Gly Leu Gln Lys Ile Leu
            125                 130                 135 aac gtg caa aaa aaa tta cca ata atc cag aaa att att atc atg gat         786
```

```
           Asn Val Gln Lys Lys Leu Pro Ile Ile Gln Lys Ile Ile Met Asp
                   140                 145                 150 tct aaa acg gat tac cag gga ttt cag tcg atg tac acg ttc gtc aca      834
Ser Lys Thr Asp Tyr Gln Gly Phe Gln Ser Met Tyr Thr Phe Val Thr
155                 160                 165 tct cat cta cct ccc ggt ttt aat gaa tac gat ttt gta cca gag tcc      882
Ser His Leu Pro Pro Gly Phe Asn Glu Tyr Asp Phe Val Pro Glu Ser
170                 175                 180                 185 ttt gat cgt gac aaa aca att gca ctg ata atg aat tcc tct gga tct      930
Phe Asp Arg Asp Lys Thr Ile Ala Leu Ile Met Asn Ser Ser Gly Ser
                190                 195                 200 act ggg tta cct aag ggt gtg gcc ctt ccg cat aga act gcc tgc gtc      978
Thr Gly Leu Pro Lys Gly Val Ala Leu Pro His Arg Thr Ala Cys Val
            205                 210                 215 aga ttc tcg cat gcc aga gat cct att ttt ggc aat caa atc att ccg     1026
Arg Phe Ser His Ala Arg Asp Pro Ile Phe Gly Asn Gln Ile Ile Pro
        220                 225                 230 gat act gcg att tta agt gtt gtt cca ttc cat cac ggt ttt gga atg     1074
Asp Thr Ala Ile Leu Ser Val Val Pro Phe His His Gly Phe Gly Met
    235                 240                 245 ttt act aca ctc gga tat ttg ata tgt gga ttt cga gtc gtc tta atg     1122
Phe Thr Thr Leu Gly Tyr Leu Ile Cys Gly Phe Arg Val Val Leu Met
250                 255                 260                 265 tat aga ttt gaa gaa gag ctg ttt tta cga tcc ctt cag gat tac aaa     1170
Tyr Arg Phe Glu Glu Glu Leu Phe Leu Arg Ser Leu Gln Asp Tyr Lys
                270                 275                 280 att caa agt gcg ttg cta gta cca acc cta ttt tca ttc ttc gcc aaa     1218
Ile Gln Ser Ala Leu Leu Val Pro Thr Leu Phe Ser Phe Phe Ala Lys
            285                 290                 295 agc act ctg att gac aaa tac gat tta tct aat tta cac gaa att gct     1266
Ser Thr Leu Ile Asp Lys Tyr Asp Leu Ser Asn Leu His Glu Ile Ala
        300                 305                 310 tct ggg ggc gca cct ctt tcg aaa gaa gtc ggg gaa gcg gtt gca aaa     1314
Ser Gly Gly Ala Pro Leu Ser Lys Glu Val Gly Glu Ala Val Ala Lys
    315                 320                 325 cgc ttc cat ctt cca ggg ata cga caa gga tat ggg ctc act gag act     1362
Arg Phe His Leu Pro Gly Ile Arg Gln Gly Tyr Gly Leu Thr Glu Thr
330                 335                 340                 345 aca tca gct att ctg att aca ccc gag ggg gat gat aaa ccg ggc gcg     1410
Thr Ser Ala Ile Leu Ile Thr Pro Glu Gly Asp Asp Lys Pro Gly Ala
                350                 355                 360 gtc ggt aaa gtt gtt cca ttt ttt gaa gcg aag gtt gtg gat ctg gat     1458
Val Gly Lys Val Val Pro Phe Phe Glu Ala Lys Val Val Asp Leu Asp
            365                 370                 375 acc ggg aaa acg ctg ggc gtt aat cag aga ggc gaa tta tgt gtc aga     1506
Thr Gly Lys Thr Leu Gly Val Asn Gln Arg Gly Glu Leu Cys Val Arg
        380                 385                 390 gga cct atg att atg tcc ggt tat gta aac aat ccg gaa gcg acc aac     1554
Gly Pro Met Ile Met Ser Gly Tyr Val Asn Asn Pro Glu Ala Thr Asn
    395                 400                 405 gcc ttg att gac aag gat gga tgg cta cat tct gga gac ata gct tac     1602
Ala Leu Ile Asp Lys Asp Gly Trp Leu His Ser Gly Asp Ile Ala Tyr
410                 415                 420                 425 tgg gac gaa gac gaa cac ttc ttc ata gtt gac cgc ttg aag tct tta     1650
Trp Asp Glu Asp Glu His Phe Phe Ile Val Asp Arg Leu Lys Ser Leu
                430                 435                 440 att aaa tac aaa gga tat cag gtg gcc ccc gct gaa ttg gaa tcg ata     1698
Ile Lys Tyr Lys Gly Tyr Gln Val Ala Pro Ala Glu Leu Glu Ser Ile
            445                 450                 455 ttg tta caa cac ccc aac atc ttc gac gcg ggc gtg gca ggt ctt ccc     1746
```

```
                                                                   -continued
Leu Leu Gln His Pro Asn Ile Phe Asp Ala Gly Val Ala Gly Leu Pro
        460                 465                 470 gac gat gac gcc ggt gaa ctt ccc gcc gcc gtt gtt gtt ttg gag cac      1794
Asp Asp Asp Ala Gly Glu Leu Pro Ala Ala Val Val Val Leu Glu His
        475                 480                 485 gga aag acg atg acg gaa aaa gag atc gtg gat tac gtg gcc agt caa      1842
Gly Lys Thr Met Thr Glu Lys Glu Ile Val Asp Tyr Val Ala Ser Gln
490                 495                 500                 505 gta aca acc gcg aaa aag ttg cgc gga gga gtt gtg ttt gtg gac gaa      1890
Val Thr Thr Ala Lys Lys Leu Arg Gly Gly Val Val Phe Val Asp Glu
                510                 515                 520 gta ccg aaa ggt ctt acc gga aaa ctc gac gca aga aaa atc aga gag      1938
Val Pro Lys Gly Leu Thr Gly Lys Leu Asp Ala Arg Lys Ile Arg Glu
            525                 530                 535 atc ctc ata aag gcc aag aag ggc gga aag tcc aaa ttg taa              1980
Ile Leu Ile Lys Ala Lys Lys Gly Gly Lys Ser Lys Leu
            540                 545                 550 aatgtaactg tattcagcga tgacgaaatt cttagctatt gtaatactgc gatgagtggc    2040
agggcggggc gtaatttttt taaggcagtt attggtgccc ttaaacgcct ggtgctacgc    2100
ctgaataagt gataataagc ggatgaatgg cagaaattcg ccggatcttt gtgaaggaac    2160
cttacttctg tggtgtgaca taattggaca aactacctac agagatttaa agctctaagg    2220
taaatataaa attttaagt gtataatgtg ttaaactact gattctaatt gtttgtgtat     2280
tttagattcc aacctatgga actgatgaat gggagcagtg gtggaatgcc tttaatgagg    2340
aaaacctgtt ttgctcagaa gaaatgccat ctagtgatga tgaggctact gctgactctc    2400
aacattctac tcctccaaaa agaagagaa aggtagaaga ccccaaggac tttccttcag     2460
aattgctaag ttttttgagt catgctgtgt ttagtaatag aactcttgct tgctttgcta    2520
tttacaccac aaaggaaaaa gctgcactgc tatacaagaa aattatggaa aaatattctg    2580
taacctttat aagtaggcat aacagttata atcataacat actgtttttt cttactccac    2640
acaggcatag agtgtctgct attaataact atgctcaaaa attgtgtacc tttagctttt    2700
taatttgtaa aggggttaat aaggaatatt tgatgtatag tgccttgact agagatcata    2760
atcagccata ccacatttgt agaggttta cttgctttaa aaaacctccc acacctcccc     2820
ctgaacctga acataaaat gaatgcaatt gttgttgtta acttgtttat tgcagcttat     2880
aatggttaca ataaagcaa tagcatcaca aatttcacaa ataaagcatt tttttcactg     2940
cattctagtt gtggttttgtc caaactcatc aatgtatctt atcatgtctg gatccgtcga   3000
ccgatgccct tgagagcctt caacccagtc agctccttcc ggtgggcgcg gggcatgact    3060
atcgtcgccg cacttatgac tgtcttcttt atcatgcaac tcgtaggaca ggtgccggca    3120
gcgctcttcc gcttcctcgc tcactgactc gctgcgctcg gtcgttcggc tgcggcgagc    3180
ggtatcagct cactcaaagg cggtaatacg gttatccaca gaatcagggg ataacgcagg    3240
aaagaacatg tgagcaaaag gccagcaaaa ggccaggaac cgtaaaaagg ccgcgttgct    3300 ggcgttttc ataggctcc gcccccctga cgagcatcac aaaaatcgac gctcaagtca     3360
gaggtggcga aacccgacag gactataaag ataccaggcg tttccccctg gaagctccct    3420
cgtgcgctct cctgttccga ccctgccgct taccggatac ctgtccgcct ttctcccttc    3480
gggaagcgtg gcgctttctc aatgctcacg ctgtaggtat ctcagttcgg tgtaggtcgt    3540
tcgctccaag ctgggctgtg tgcacgaacc ccccgttcag cccgaccgct gcgccttatc    3600
cggtaactat cgtcttgagt ccaacccggt aagacacgac ttatcgccac tggcagcagc    3660
cactggtaac aggattagca gagcgaggta tgtaggcggt gctacagagt tcttgaagtg    3720
```

```
gtggcctaac tacggctaca ctagaaggac agtatttggt atctgcgctc tgctgaagcc    3780
agttaccttc ggaaaaagag ttggtagctc ttgatccggc aaacaaacca ccgctggtag    3840
cggtggtttt tttgtttgca agcagcagat tacgcgcaga aaaaaaggat ctcaagaaga    3900
tcctttgatc ttttctacgg ggtctgacgc tcagtggaac gaaaactcac gttaagggat    3960
tttggtcatg agattatcaa aaaggatctt cacctagatc cttttaaatt aaaaatgaag    4020
ttttaaatca atctaaagta tatatgagta aacttggtct gacagttacc aatgcttaat    4080
cagtgaggca cctatctcag cgatctgtct atttcgttca tccatagttg cctgactccc    4140
cgtcgtgtag ataactacga tacgggaggg cttaccatct ggccccagtg ctgcaatgat    4200
accgcgagac ccacgctcac cggctccaga tttatcagca ataaaccagc cagccggaag    4260
ggccgagcgc agaagtggtc ctgcaacttt atccgcctcc atccagtcta ttaattgttg    4320
ccgggaagct agagtaagta gttcgccagt taatagtttg cgcaacgttg ttgccattgc    4380
tacaggcatc gtggtgtcac gctcgtcgtt tggtatggct tcattcagct ccggttccca    4440
acgatcaagg cgagttacat gatcccccat gttgtgcaaa aaagcggtta gctccttcgg    4500
tcctccgatc gttgtcagaa gtaagttggc cgcagtgtta tcactcatgg ttatggcagc    4560
actgcataat tctcttactg tcatgccatc cgtaagatgc ttttctgtga ctggtgagta    4620
ctcaaccaag tcattctgag aatagtgtat gcggcgaccg agttgctctt gcccggcgtc    4680
aatacgggat aataccgcgc cacatagcag aactttaaaa gtgctcatca ttggaaaacg    4740
ttcttcgggg cgaaaactct caaggatctt accgctgttg agatccagtt cgatgtaacc    4800
cactcgtgca cccaactgat cttcagcatc ttttactttc accagcgttt ctgggtgagc    4860
aaaaacagga aggcaaaatg ccgcaaaaaa gggaataagg gcgacacgga aatgttgaat    4920
actcatactc ttcctttttc aatattattg aagcatttat cagggttatt gtctcatgag    4980
cggatacata tttgaatgta tttagaaaaa taaacaaata ggggttccgc gcacatttcc    5040
ccgaaaagtg ccacctgacg cgccctgtag cggcgcatta agcgcggcgg gtgtggtggt    5100
tacgcgcagc gtgaccgcta cacttgccag cgccctagcg cccgctcctt tcgctttctt    5160
cccttccttt ctcgccacgt tcgccggctt tccccgtcaa gctctaaatc ggggggctccc    5220
tttagggttc cgatttagtg ctttacggca cctcgacccc aaaaaacttg attagggtga    5280
tggttcacgt agtgggccat cgccctgata gacggttttt cgccctttga cgttggagtc    5340
cacgttcttt aatagtggac tcttgttcca aactggaaca acactcaacc ctatctcggt    5400
ctattctttt gatttataag ggattttgcc gatttcggcc tattggttaa aaaatgagct    5460
gatttaacaa aaatttaacg cgaattttaa caaatatta cgtttacaa tttcccattc    5520
gccattcagg ctgcgcaact gttgggaagg gcgatcggtg cgggcctctt cgctattacg    5580
ccagcccaag ctaccatgat aagtaagtaa tattaaggta cgtggaggtt ttacttgctt    5640
taaaaaacct cccacacctc cccctgaacc tgaaacataa aatgaatgca attgttgttg    5700
ttaacttgtt tattgcagct tataatggtt acaaataaag caatagcatc acaaatttca    5760
caaataaagc atttttttca ctgcattcta gttgtggttt gtccaaactc atcaatgtat    5820
cttatggtac tgtaactgag ctaacataa                                     5849
```

<210> SEQ ID NO 2  
<211> LENGTH: 550  
<212> TYPE: PRT  
<213> ORGANISM: Artificial  
<220> FEATURE:  
<223> OTHER INFORMATION: Synthetic Construct

```
<400> SEQUENCE: 2

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415
```

```
Trp Leu His Ser Gly Asp Ile Ala Tyr Trp Asp Glu Asp His Phe
            420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                    485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Ile Lys Ala Lys Lys
            530                 535                 540
Gly Gly Lys Ser Lys Leu
545                 550

<210> SEQ ID NO 3
<211> LENGTH: 4412
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (358)..(1077)

<400> SEQUENCE: 3
tagttattac tagcgctacc ggactcagac tcgggaaagg gaaaccgaaa ctgaagcccc      60
tcgggaaagg gaaaccgaaa ctgaagcccg atctgcatct caattagtca gcaaccatag    120
tcccgcccct aactccgccc atcccgcccc taactccgcc cagttccgcc cattctccgc    180
cccatggctg actaattttt tttatttatg cagaggccga ggccgcctcg gcctctgagc    240
tattccagaa gtagtgagga ggcttttttg gaggcctagg cttttgcaaa tctcgagctc    300
aagcttcgaa ttctgcagtc gacggtaccg cgggcccggg atccaccggt cgccacc       357 atg gtg agc aag ggc gag gag ctg ttc acc ggg gtg gtg ccc atc ctg      405
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      453
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc      501
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc      549
Cys Thr Thr Gly Lys Leu Pro Val Pro Trp Pro Thr Leu Val Thr Thr
        50                  55                  60 ctg acc tac ggc gtg cag tgc ttc agc cgc tac ccc gac cac atg aag      597
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag      645
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag      693
Arg Thr Ile Phe Phe Lys Asp Asp Gly Asn Tyr Lys Thr Arg Ala Glu
                100                 105                 110
```

```
gtg aag ttc gag ggc gac acc ctg gtg aac cgc atc gag ctg aag ggc        741
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac        789
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        837
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        885
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        933
Val Gln Leu Ala Asp His Tyr Gln Gln Asn Thr Pro Ile Gly Asp Gly
        180                 185                 190 ccc gtg ctg ctg ccc gac aac cac tac ctg agc acc cag tcc gcc ctg        981
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc       1029
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag taa       1077
Val Thr Ala Ala Gly Ile Thr Leu Gly Met Asp Glu Leu Tyr Lys
225                 230                 235 agcggccgcg actctagatc ataatcagcc ataccacatt tgtagaggtt ttacttgctt     1137 taaaaacct  cccacacctc ccctgaacc  tgaaacataa aatgaatgca attgttgttg     1197
ttaacttgtt tattgcagct tataatggtt acaaataaag caatagcatc acaaatttca     1257
caaataaagc attttttca  ctgcattcta gttgtggttt gtccaaactc atcaatgtat     1317
cttaaggcgt aaattgtaag cgttaatatt tgttaaaat  tcgcgttaaa ttttttgttaa    1377 atcagctcat tttttaacca ataggccgaa atcggcaaaa tcccttataa atcaaaagaa     1437
tagaccgaga tagggttgag tgttgttcca gtttggaaca agagtccact attaaagaac     1497
gtggactcca acgtcaaagg gcgaaaaacc gtctatcagg gcgatggccc actacgtgaa     1557
ccatcaccct aatcaagttt tttggggtcg aggtgccgta aagcactaaa tcggaaccct     1617
aaagggagcc cccgatttag agcttgacgg ggaaagccgg cgaacgtggc gagaaaggaa     1677
gggaagaaag cgaaaggagc gggcgctagg gcgctggcaa gtgtagcggt cacgctgcgc     1737
gtaaccacca cacccgccgc gcttaatgcg ccgctacagg gcgcgtcagg tggcactttt     1797
cggggaaatg tgcgcggaac ccctatttgt ttattttct  aaatacattc aaatatgtat     1857
ccgctcatga caataaacc  ctgataaatg cttcaataat attgaaaaag gaagagtcct     1917
gaggcggaaa gaaccagctg tggaatgtgt gtcagttagg gtgtggaaag tccccaggct     1977
ccccagcagg cagaagtatg caaagcatgc atctcaatta gtcagcaacc aggtgtggaa     2037
agtccccagg ctccccagca ggcagaagta tgcaaagcat gcatctcaat tagtcagcaa     2097
ccatagtccc gcccctaact ccgcccatcc cgccctaac  tccgcccagt tccgcccatt     2157
ctccgcccca tggctgacta atttttttta tttatgcaga ggccgaggcc gcctcggcct     2217
ctgagctatt ccagaagtag tgaggaggct ttttggagg  cctaggcttt tgcaaagatc     2277
gatcaagaga caggatgagg atcgtttcgc atgattgaac aagatggatt gcacgcaggt     2337
tctccggccg cttgggtgga gaggctattc ggctatgact gggcacaaca gacaatcggc     2397
tgctctgatg ccgccgtgtt ccggctgtca gcgcaggggc gcccggttct ttttgtcaag     2457
accgacctgt ccggtgccct gaatgaactg caagacgagg cagcgcggct atcgtggctg     2517
```

```
gccacgacgg gcgttccttg cgcagctgtg ctcgacgttg tcactgaagc gggaagggac    2577
tggctgctat tgggcgaagt gccggggcag gatctcctgt catctcacct tgctcctgcc    2637
gagaaagtat ccatcatggc tgatgcaatg cggcggctgc atacgcttga tccggctacc    2697
tgcccattcg accaccaagc gaaacatcgc atcgagcgag cacgtactcg gatggaagcc    2757
ggtcttgtcg atcaggatga tctggacgaa gagcatcagg ggctcgcgcc agccgaactg    2817
ttcgccaggc tcaaggcgag catgcccgac ggcgaggatc tcgtcgtgac ccatggcgat    2877
gcctgcttgc cgaatatcat ggtggaaaat ggccgctttt ctggattcat cgactgtggc    2937
cggctgggtg tggcggaccg ctatcaggac atagcgttgg ctacccgtga tattgctgaa    2997
gagcttggcg gcgaatgggc tgaccgcttc ctcgtgcttt acggtatcgc cgctcccgat    3057
tcgcagcgca tcgccttcta tcgccttctt gacgagttct tctgagcggg actctggggt    3117
tcgaaatgac cgaccaagcg acgcccaacc tgccatcacg agatttcgat tccaccgccg    3177
ccttctatga aaggttgggc ttcggaatcg ttttccggga cgccggctgg atgatcctcc    3237
agcgcgggga tctcatgctg gagttcttcg cccacccctag ggggaggcta actgaaacac    3297
ggaaggagac aataccggaa ggaacccgcg ctatgacggc aataaaaaga cagaataaaa    3357
cgcacggtgt tgggtcgttt gttcataaac gcggggttcg gtcccagggc tggcactctg    3417 tcgataccc accgagaccc cattggggcc aatacgcccg cgtttcttcc ttttccccac    3477
cccacccccc aagttcgggt gaaggcccag ggctcgcagc caacgtcggg gcggcaggcc    3537
ctgccatagc ctcaggttac tcatatatac tttagattga tttaaaactt cattttaat    3597 ttaaaaggat ctaggtgaag atcctttttg ataatctcat gaccaaaatc ccttaacgtg    3657
agttttcgtt ccactgagcg tcagacccc g tagaaaagat caaaggatct tcttgagatc    3717 cttttttct gcgcgtaatc tgctgcttgc aaacaaaaaa accaccgcta ccagcggtgg    3777
tttgtttgcc ggatcaagag ctaccaactc tttttccgaa ggtaactggc ttcagcagag    3837
cgcagatacc aaatactgtc cttctagtgt agccgtagtt aggccaccac ttcaagaact    3897
ctgtagcacc gcctacatac ctcgctctgc taatcctgtt accagtggct gctgccagtg    3957
gcgataagtc gtgtcttacc gggttggact caagacgata gttaccggat aaggcgcagc    4017
ggtcgggctg aacggggggt tcgtgcacac agcccagctt ggagcgaacg acctacaccg    4077
aactgagata cctacagcgt gagctatgag aaagcgccac gcttcccgaa gggagaaagg    4137
cggacaggta tccggtaagc ggcagggtcg aacaggaga gcgcacgagg gagcttccag    4197 gggaaacgc ctggtatctt tatagtcctg tcgggtttcg ccacctctga cttgagcgtc    4257
gatttttgtg atgctcgtca ggggggcgga gcctatggaa aaacgccagc aacgcggcct    4317
ttttacggtt cctggccttt tgctggcctt ttgctcacat gttctttcct gcgttatccc    4377
ctgattctgt ggataaccgt attaccgcca tgcat                              4412
```

<210> SEQ ID NO 4
<211> LENGTH: 239
<212> TYPE: PRT
<213> ORGANISM: Artificial
<220> FEATURE:
<223> OTHER INFORMATION: Synthetic Construct

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

```
<210> SEQ ID NO 5
<211> LENGTH: 60
<212> TYPE: DNA
<213> ORGANISM: Artificial
<220> FEATURE:
<223> OTHER INFORMATION: Synthetic

<400> SEQUENCE: 5
ctcgggaaag ggaaaccgaa actgaagccc ctcgggaaag ggaaaccgaa actgaagccc    60

<210> SEQ ID NO 6
<211> LENGTH: 15
<212> TYPE: DNA
<213> ORGANISM: Artificial
<220> FEATURE:
<223> OTHER INFORMATION: Synthetic

<400> SEQUENCE: 6
ggraaagwga aactg                                                     15

<210> SEQ ID NO 7
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is either a, c, g, or t.
<220> FEATURE:
<221> NAME/KEY: misc_feature
<222> LOCATION: (6)..(6)
<223> OTHER INFORMATION: n is either a, c, g, or t.
<220> FEATURE:
```

```
<221> NAME/KEY: misc_feature
<222> LOCATION: (16)..(16)
<223> OTHER INFORMATION: n is either a, c, g, or t.
<220> FEATURE:
<221> NAME/KEY: misc_feature
<222> LOCATION: (19)..(19)
<223> OTHER INFORMATION: n is either a, c, g, or t.
<220> FEATURE:
<221> NAME/KEY: misc_feature
<222> LOCATION: (21)..(21)
<223> OTHER INFORMATION: n is either a, c, g, or t.

<400> SEQUENCE: 7
nnnsanttcc gggaantgns n                                          21

<210> SEQ ID NO 8
<211> LENGTH: 29
<212> TYPE: DNA
<213> ORGANISM: Artificial
<220> FEATURE:
<223> OTHER INFORMATION: synthetic

<400> SEQUENCE: 8
ctcgggaaag ggaaaccgaa actgaagcc                                  29
```

METHOD FOR CONDUCTING AN ASSAY FOR NEUTRALIZING ANTIBODIES

CROSS-REFERENCE TO RELATED APPLICATIONS

This application claims the benefit of priority from U.S. provisional application No. 60/983,813, filed Oct. 30, 2007, the entire content of which is herein incorporated by reference.

BACKGROUND OF THE INVENTION

1. Field of the Invention

The present invention relates to a gene reporter assay and a kit for determining the presence and/or the level in a sample of a molecule that activates the signal transduction activity of a cell surface protein. The present invention further relates to a cell which can be used in such an assay and to a method for preparing such a cell.

2. Description of the Related Art

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as cytokines, growth factors, certain hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals indirectly alter gene expression by activating the expression of genes, such as immediate-early genes that encode regulatory proteins, which in turn activate expression of other genes that encode transcriptional regulatory proteins. Other extracellular signal molecules cause activation of latent cytoplasmic signal transducers and activators of transcription (STAT) protein that enhance the transcription of specific sets of genes.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell Surface Receptors

Cell surface-localized receptors are membrane spanning proteins that bind extracellular signalling molecules or detect changes in the extracellular environment and transmit the signal via signal transduction pathways to effect a cellular response. Cell surface receptors bind circulating signal molecules, such as cytokines, growth factors and hormones, etc., as the initiating step in the activation of numerous intracellular pathways. Receptors are classified on a structural basis or on the basis of the particular type of pathway that is induced. Among these classes of receptors are classes of cytokine receptors which include those that bind growth factors and have intrinsic tyrosine kinase activity, such as the heparin binding growth factor (HBGF) receptors, the immunoglobulin receptor superfamily, the hematopoietin/cytokine receptor superfamily, the nerve-growth factor receptor superfamily, other receptor tyrosine or serine kinases, and those that couple to effector proteins through guanine nucleotide binding regulatory proteins, which are referred to as G protein coupled receptors and G proteins, respectively.

Cytokines are intercellular messengers which coordinate communication between cells within a particular tissue, for example, antibody and T cell immune system interactions, and serve to modulate or modify the biological response. They are pleiotropic and have a broad spectrum of biological effects on more than one type of cell or tissue. The receptors for cytokines are broadly grouped into two classes, where the Class I cytokine receptors include receptors that bind various interleukins (IL-2, IL-3, IL-4, IL-6, IL-7, IL-9, IL-11, IL-12, IL-15), erythropoietin (EPO), growth hormone (GH), granulocyte colony stimulating factor (G-CSF), granulocyte macrophage colony stimulating factor (GM-CSF), leukemia inhibitory factor (LIF), and ciliary neurotrophic factor (CNTF), TNF$\alpha$, TGF$\beta$, Fas-ligand, and the Class II cytokine receptors include receptors that bind interferon (IFN) $\alpha/\beta$, IFN$\gamma$, and IL-10.

Interferon Receptors

Human interferons (IFNs) are a family of homologous helical cytokines composed of three distinct classes: type I, type II, and type III based on nucleotide and amino acid sequence homology. Human Type I IFNs consist of IFN-$\alpha$, IFN-$\beta$, IFN-$\epsilon$, IFN-$\kappa$, and IFN-$\omega$). Human IFN-$\alpha$ includes a group of closely related proteins encoded by at least 12 functional IFN-$\alpha$ genes. IFN-$\beta$, IFN-$\epsilon$, IFN-$\kappa$, and IFN-$\omega$, are encoded by single more distantly related genes. Type II IFN, or IFN$\gamma$, is encoded by an unrelated gene and binds to a distinct cell surface receptor (De Maeyer et al., 1988; Pestka et al., 1987 and Diaz et al., 1993). Recently, a novel group of interferons designated IFN-$\lambda$ or type III IFNs has been described. The group has three members IFN-$\lambda$1, IFN-$\lambda$2, and IFN-$\lambda$3 also termed interleukin-29 (IL-29)($\lambda$1), and IL-28A/B ($\lambda$2/3). (Sheppard et al., 2003; and Ank et al., 2006).

Type I IFNs bind to a common receptor, as shown by their ability to cross-compete for receptor binding (Pestka et al., 1987; Branca et al., 1981; and Merlin et al., 1985). The Type 1 interferon receptor has the largest number of natural ligands, some 14 in all, of all known cytokine receptors. Binding of interferons to their cell surface receptor represents the initial and probably most specific step in the IFN signaling pathway.

The Type I IFN receptor is composed of two transmembrane glycoproteins, IFNAR1 and IFNAR2 (Uze et al., 1990; Novick et al., 1994; Lutfalla et al., 1995; Domanski et al., 1995), which are rapidly tyrosine-phosphorylated following IFN binding (Platanias et al., 1994; Constantinescu et al., 1994; and Abramovich et al., 1994). Both subunits belong to the class II cytokine receptor superfamily (Bazan et al., 1990 and Thoreau et al., 1990) and are required for high affinity ligand binding and the establishment of biological activity (Langer et al., 1996 and Domanski et al., 1996). Class II cytokine receptors are distinguished from Class I receptors on the basis of the pattern of the conserved pairs of cysteine residues that are thought to form disulfide bonds.

The Type II IFN (IFN $\gamma$) receptor is composed of two transmembrane glycoproteins, IFNGR1 and IFNGR2 that are preassembled at the cell surface. Binding of IFN $\gamma$ to its receptor activates the tyrosine kinases Jak1 and Jak2 resulting in tyrosine-phosphorylation and formation of a Stat1 homodimer. The activated Stat1 homodimer is then translocated to the nucleus where it binds to the GAS (Gamma Activated Sequence) resulting in transcriptional activation of IFN γ activated genes.

Type III interferons bind to a unique receptor comprising the IL-28Rα, which is specific for chain the IFN-λs, and the IL-10Rβ chain which is also part of the receptors for IL-10, IL-22, and IL-26 (Ank et al, 2006).

In contrast to other cytokine receptors, particularly the IFN-γ receptor, neither IFNAR1 nor IFNAR2 alone bind to IFNα or IFNβ with an affinity comparable to the heterodimer. Despite the fact that IFNAR2 plays a prominent role in ligand binding, IFNAR1 contributes to IFN binding by increasing the affinity of the receptor complex (4-10 fold) relative to that of IFNAR2 alone. IFNAR1 also modulates the specificity of ligand binding relative to that observed with IFNAR2 alone (Cohen et al., 1995; Russell-Harde et al., 1995; Cutrone et al., 1997; and Cook et al., 1996). IFNAR1 has a larger extracellular domain than most other class II cytokine receptors, composed of 4 immunoglobulin-like subdomains separated by di- or tri-proline motifs which can be divided into two tandem repeats (Novick et al., 1994; Lutfalla et al., 1992; and Uzé et al., 1995).

Human, murine and bovine IFNAR1 have been cloned and expressed in human and murine cells. Studies performed with transfected cells show that IFNAR1 plays a central role in ligand binding, cellular responses to IFNs and in the induction of the biological activities of the Type I interferons (Novick et al., 1994; Abramovich et al., 1994; Uze et al., 1992; Mouchel-Vielh et al., 1992; Lim et al., 1993; Cleary et al., 1994; Constantinescu et al., 1995; Hwang et al., 1995; Vandenbroek et al., 1995; and Colamonici et al., 1994). The IFN receptor also determines the high degree of species specificity characteristic of the IFNs. Thus, transfection of mouse cells with IFNAR1 and IFNAR2 renders mouse cells sensitive to human type I IFNs since both human and mouse cells share a common signaling pathway and common IFN responsive elements in the promoter regions of IFN regulated genes. Furthermore, the intracellular domain of IFNAR1 has been shown to play a key role in the transduction of the signal initiated at the cell surface to the nucleus following binding of Type I interferons (Basu et al., 1998). Targeted disruption of the IFNAR1 gene results in the loss of the antiviral response to Type I IFNs demonstrating that this receptor polypeptide is an essential component of the receptor complex and that both IFNAR1 and IFNAR2 subunits are required for IFNα and IFNβ signaling (Vandenbroek et al., 1995; Muller et al., 1994; Fiette et al., 1995; Steinhoff et al., 1995; and van den Broek et al., 1995).

Binding of type I interferon to the receptor complex activates two Janus kinases, Tyk2 and JAK1, which mediate the tyrosine phosphorylation and activation of two latent cytoplasmic transcription factors STAT1 and STAT2 which form a complex (ISGF3) with a p48 DNA binding protein, interferon responsive protein 9 (IRF 9), which is translocated to the nucleus to promote specific gene transcription (Fu et al., 1992; Schindler et al., 1992; Darnell et al., 1994; Ihle et al, 1995; and Taniguchi, 1995). Both Tyk2 and STAT2 are constitutively associated with the membrane proximal region of the IFNAR1 chain, while JAK1 and STAT1 are physically associated with IFNAR2 and all four factors are rapidly activated during IFNα stimulation (Lutfalla et al., 1995; Bazan, 1990; Basu et al., 1998; Barbieri et al., 1994; Velazquez et al., 1995; Uddin et al., 1995; Yan et al., 1996(a) and 1996(b).

Binding of type III IFNs to their cell-surface receptor also activates the ISGF3 complex suggesting that type III IFNs also activate a number of genes in common with type I IFNs (Ank et al., 2006).

Pattern Recognition Receptors

Key populations of cells including DCs distributed throughout the peripheral tissues act as sentinels capable of recognizing infectious agents through pattern-recognition receptors (PRR). These include the Toll-like receptor (TLR) family of cell surface and endosomal membrane receptors (Uematsu and Akira, 2007) and the retinoic acid-inducible gene I (RIG-I)-like cytosoloic receptor proteins RIG-I, MDA5, and LGP2 (Yoneyama and Fujita, 2007). Thirteen members of the TLR family have been identified in mammals (Uematsu and Akira, 2007). Each TLR mediates a distinctive response in association with different combinations of four Toll/IL-1 receptor (TIR) domain-containing adaptor proteins (MyD88, TRIF, TIRAP/MAL, and TRAM). All the TLRs except TLR3 interact with MyD88. TLR3, which recognizes single-stranded or double-stranded viral RNA, is localized in the endosomes of myeloid DCs and requires acidification of vesicles for activation. TLR3 signals via TRIF and activates TBK1/IKKe which phosphorylates the interferon regulatory factor 3 (IRF3) and NFkB, resulting in production of IFN b (Hemmi et al, 2004, Perry et al., 2004). The RIG-I-like receptor proteins are DExD/H box RNA helicases two of which, RIG-I and MDA5, carry caspase activation and recruitment domain (CARD)-like motifs at the N-terminus (Yoneyama and Fujita, 2007). The CARD domain interacts with IPS-1 resulting in activation of IRF3 and NFkB and production of IFN b. Thus, activation of PRRs leads to the production of pro-inflammatory cytokines including type I IFNs and activation of the innate immune response.

Dendritic cells signal principally through TLRs while RIG-I-like receptors predominate in other cell types. Two major DC sub-sets can be distinguished in man, CD11c(+) monocyte derived myeloid DCs, present in most tissues, and CD11c(−) plasmacytoid DCs (pDCs), present principally in lymph nodes. Plasmacytoid DCs are the principal producers of type I IFNs in response to viruses (Steinmann and Hemmi, 2006). Plasmacytoid DCs express high levels of TLR7/8 and TLR9 that recognize single-stranded RNA (ssRNA) and CpG DNA respectively (Diebold et al., 2004, Heli et al., 2004). Hemmi et al., 2000). Activation of both TLR7/8 and TLR9 leads to the formation of a complex with MyD88 and phosphorylation of IRF7 and production of high levels of type I IFNs (Uematsu and Akira, 2007).

TNF Receptors

Tumor necrosis factor alpha (TNF-α) is a multifunctional cytokine that exerts pleiotropic effects on different cell types. TNF-α is synthesized as pro-TNF, a 26 kDa membrane bound protein, which is released upon cleavage of its pro domain by TNF-converting enzyme (TACE) to yield a 17 kDa protein consisting of 157 amino acids that exists as a homotrimer in solution. TNF-α bind to two distinct receptors TNFR-1 (p55) and TNFR2 (p75). TNFR1 contains a death domain (absent from TNFR2) which is involved in the induction of apoptosis. Binding of the TNF-α homotrimer to TNFR-1 results in trimerization of TNFR-1 and the silencer of death domain (SODD) is released. The TNFR-associated death domain (TRADD) binds to the death domain of TNFR-1 and recruits the adaptor proteins, receptor interacting protein (RIP), TNFR-associated factor 2 (TRAF-2), and the Fas-associated death domain (FADD). TNFR-1 signals apoptosis, by FADD binding pro-caspase-8 the activation of which leads to induction of a protease cascade resulting in apoptosis. TNFR-1 signals survival by recruitment of TRAF-2 which inhibits apoptosis via the cytoplasmic inhibitor of apoptosis protein (cIAP). One of the principal signaling pathways triggered by recruitment of TRAF-2 and RIP to the TNFR-1 receptor complex is the NF-κB pathway which transduces a signal to the nucleus culminating in transcriptional activation of a number of TNF target genes (Schwamborn et al., 2003). NF-κB is a ubiquitous transcription factor induced by a number of cytokines (including IFNγ, IL2, IL5 and IFNα2). NF-κB is involved in the regulation of numerous genes involved in processes including, the inflammatory response, apoptosis, cancer, neuronal survival, and innate immunity. Activation of NF-κB is controlled principally at the posttranscriptional level by degradation of the inhibitory subunit IκB of the p55/p65/IκB complex present in the cytoplasm. Activating stimuli such as TNFα activate a kinase complex composed of two IκB-specific kinases (IKKα and IKKβ) and a modulatory subunit (NEMO or IKKγ). This leads to phosphorylation of the inhibitory subunit, which is then ubiquitinylated and degraded via the proteasome. This triggers translocation of NF-κB into the nucleus, where it initiates transcription by binding to regulatory sequences (NF-κB recognition/binding sequences) present in the promoter region of NF-κB target genes.

G-Coupled Receptors

The G protein transmembrane signaling pathways consist of three proteins: receptors, G proteins and effectors. G proteins, which are the intermediaries in transmembrane signaling pathways, are heterodimers and consist of α, β and γ subunits. Among the members of a family of G proteins the α subunits differ. Functions of G proteins are regulated by the cyclic association of GTP with the α subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

Growth Factors and Growth Factor Receptors

Polypeptide growth factors are modulators of cell proliferation and differentiation whose biological functions are mediated by the interaction of the growth factor with cell surface receptors and subsequent alterations in gene expression. Growth factors bind to specific receptors and appear to induce tyrosine phosphorylation and c-fos mRNA synthesis. In addition, at least some growth factors, such as platelet-derived growth factor (Yeh et al., 1987) and heparin-binding growth factor-2 or basic fibroblast growth factor (Bouche et al., 1987), are translocated to the nucleus.

Activation of growth factor receptors by interaction with specific growth factors or with agents such as phorbol mistric acetate (PMA) activates protein kinase C, which is a family of phospholipid- and calcium-activated protein kinases. This activation results in the transcription of an array of proto-oncogene transcription factor encoding genes, including c-fos, c-myc and c-jun, proteases, protease inhibitors, including collagenase type I and plasminogen activator inhibitor, and adhesion molecules, including intercellular adhesion molecule I. Protein kinase C activation antagonizes growth factor activity by the rapid phosphorylation of growth factor receptors, which thereby decreases tyrosine kinase activity.

Growth factors and other mitogens that induce cell proliferation and cell growth are believed to play a role in tumor growth, which often carry identifiable cell surface receptors specific for growth factors and other extracellular signals.

The interaction of nerve growth factor (NGF) with its receptor is typical of the array of responses such an extracellular signal induces. NGF is a polypeptide growth hormone that is necessary for differentiation and growth of the neural crest-derived sensory neuron. NGF binds to its specific cell surface receptor and is retrogradely transported to the cell body (Changelian et al., 1989). This initiates a cascade of intracellular events, culminating in a differentiated phenotype. PC12 cells, which are a rat pheochromocytoma cell line, are used as a model for the study of NGF-mediated differentiation. When treated with NGF, PC12 cells change from replicating adrenal-chromaffin-like cells to nonreplicating, electrically excitable sympathetic-neuron-like cells.

Concomitant with the phenotypic changes, there is induction and expression of specific genes. Binding of NGF to PC12 cells induces the immediate and rapid expression of certain genes, including the c-fos, NGF1-A and NGF1-B genes, which are referred to as early genes. Such early genes are believed to encode transcriptional regulators. The NGF-1A gene product contains tandemly repeated "zinc finger" domains that are characteristic of DNA-binding proteins, and the NGF1-B protein is homologous to members of the glucocorticoid receptor family and, thus, may function as a ligand-dependent modulator of transcription. The c-fos gene product, FOS appears to function as a transcriptional regulatory molecule.

The c-fos Gene and Related Genes

As discussed above, induction of expression of the c-fos gene is an event that is common to a number of response pathways that are initiated by the activity of a variety of cell surface proteins.

The c-fos gene product, FOS, associates with the transcription activator JUN, which is the product of the c-jun gene, to form a complex that forms a transcription activation complex, AP-1. Transcription of both c-fos and c-jun is induced rapidly and transiently following stimulation. The induced mRNAs accumulate for 1-2 hours in the cytoplasm where the FOS and JUN proteins, which are short-lived, are translated and then translocated to the nucleus to form a heterodimeric protein complex that binds to the DNA regulatory element, the AP-1 binding site.

The c-fos and c-jun genes are members of gene families that encode proteins that participate in the formation of heterodimeric complexes that interact with AP-1 binding sites. Transcription factor AP-1 is composed of several protein complexes whose concentrations change upon cell stimulation. These complexes specifically interact with a seven-base core nucleotide sequence motif, that is known to be a relatively common constituent of both positive and negative transcriptional regulatory elements and that is required for both basal and induced levels of gene expression.

The gene products, FOS and JUN cooperate in the regulation of target genes that underlie many cellular and adaptive responses to the environment. They are involved in a number of neurophysiological processes.

Thus, c-fos induction involves distinct second messenger pathways that act via separate regulatory elements and that differentially modify, the resulting gene product, FOS, which in turn interacts in different ways with differentially modified JUN protein. Therefore, a multitude of extracellular events induce expression of a small number of inducible proteins that form an array of protein complexes that can differentially bind to DNA regulatory elements that contain AP-1 binding sites. Therefore, numerous cell surface proteins can act via overlapping transduction pathways and transduce extracellular signals that ultimately induce a variety of responses.

There are many assays that may rely on in vivo activity in a living cell line. One example is a cell line having an Interferon Stimulatory Response Element (ISRE) connected to a luciferase gene, or another reporter gene, so that when the cell line is subjected to the presence of interferon as an extracellular signal, the signal transduction activity of endogenous interferon cell surface receptors produces a signal that activates the ISRE, which then causes transcription of the luciferase gene. Thus, the activity of luciferase in creating light can be measured and is related to the amount of interferon which is present in the sample, and which is proportional to the amount of interferon over a particular range (Lallemand et al., 1996).

Lleonart et al. (1990) described a reporter gene assay for Type I interferon based on monkey Vero cells transfected with Type I interferon inducible mouse Mx promoter linked to the human growth hormone (hGH) gene as the reporter gene. This Type I interferon assay was developed further by transfecting monkey Vero cells with a plasmid carrying the luciferase reporter gene under the control of the Type I interferon inducible mouse Mx1 promoter (Canosi et al., 1996).

A further type of interferon reporter gene assay was developed by Hammerling et al. (1998) who used a human glioblastoma cell line transfected with a reporter gene construct of glial fibrillary acidic protein (GFAP) promoter and an *E. coli* β-galactosidase (lacZ) reporter gene. In this particular assay, it is the reduction/inhibition of β-galactosidase expression by either human Type I or Type II interferon in a selective and dose dependent manner that is measured.

The results of a number of large randomized clinical studies have shown that interferon beta (IFNβ) reduces the frequency and severity of clinical relapses, slows disease progression, and improves the quality of life in patients with relapsing-remitting multiple sclerosis (RRMS) (Clerico et al., 2007; and McCormick et al., 2004). Repeated treatment with recombinant IFNβ, however, can cause a break in immune tolerance to self-antigens in some patients, resulting in the production of neutralizing antibodies (NAB) to the recombinant protein homologue (Hartung et al., 2007; Noronha, 2007; and Namaka et al., 2006). Appearance of NABs is associated with both reduced pharmacodynamics (induction of IFNβ responsive gene products; Deisenhammer et al., 2004), and a reduced clinical response determined by either magnetic resonance imaging (MRI) or disease progression (Hartung et al., 2007; Noronha, 2007; and Namaka et al., 2006). The frequency and titers of anti-IFNβ antibodies vary as a function of the type of IFNβ preparation used to treat the patient, as well as the frequency and route of administration. Although direct comparisons among many of the studies is difficult due to the use of different neutralization assays and standards, comparative studies have shown that IFNβ-1b is more immunogenic than IFNβ-1a (Bertolotto et al., 2002) possibly due to the lower specific activity of IFNβ-1b and hence the higher protein mass injected (Antonetti et al., 2002). Amino acid differences, lack of glycosylation of recombinant IFNβ-1b compared with the native protein or currently licensed forms of IFNβ-1a, or formulation characteristics may also contribute to the immunogenicity of IFNβ-1b (Giovannoni, 2004).

Current methods for detecting the presence of neutralizing antibodies to IFNα or IFNβ are based on the inhibition of IFN activity determined using either antiviral bioassays or induction of an IFN induced protein (Deisenhammer et al., 2004). Bioassays based on the ability of IFNs to inhibit virus replication are imprecise, only two fold or greater differences can be detected, give variable results, and take several days to complete. Measurement of the induction of an IFN-induced antiviral protein such as MxA requires use of cell lines or peripheral blood, and subsequent evaluation of protein levels by ELISA or measurement of MxA mRNA levels (Deisenhammer et al., 2004).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for conducting a neutralization assay for the determination of the titer of antibodies in a sample to be tested, where the antibodies are specific for a predetermined target molecule that activates the signal transduction activity of a cell surface protein or a pattern recognition receptor or are specific for an antagonist of the predetermined target molecule. This method is an improvement over existing neutralization assays because the sensitivity of the reporter gene assay to determine neutralization is increased by the use of a cell line transformed with a reporter gene construct and having the property that it will maintain signal transduction in response to an extracellular signal generated by the target molecule for at least about one hour but will lose this signal transduction activity and undergo cellular death in no more than about 30 days at a temperature above freezing.

BRIEF DESCRIPTION OF THE DRAWINGS

In FIG. 5A, assay-ready frozen PIL5 cells (iLite Alpha Beta Assay, NeutekBio Ltd, Galway, Ireland), were thawed rapidly and incubated overnight in duplicate with serial ten-fold dilutions of human IFNα2a (ROFERON-A™), IFNα2b (IN-TRON-A™), pegylated IFNα2a (PEGASYS™), or pegylated IFNα2b (PEG-INTRON™). In FIG. 5B, assay-ready frozen PIL5 cells (iLite Alpha Beta Assay, NeutekBio Ltd, Galway, Ireland), were thawed rapidly and incubated overnight in duplicate with serial ten-fold dilutions of human IFNβ-1a (AVONEX), IFNβ1a (REBIF), or IFNβ-1b (BE-TAFERON). Cells were then lysed with the luciferase substrate containing reagent and luciferase activity was determined using a luminometer as described in the Materials and Methods of Example 2. IFN activity was determined from the dose-response curve of relative luciferase units (RLU) against IFN concentration expressed as IU/ml.

DETAILED DESCRIPTION OF THE INVENTION

Figure 1:
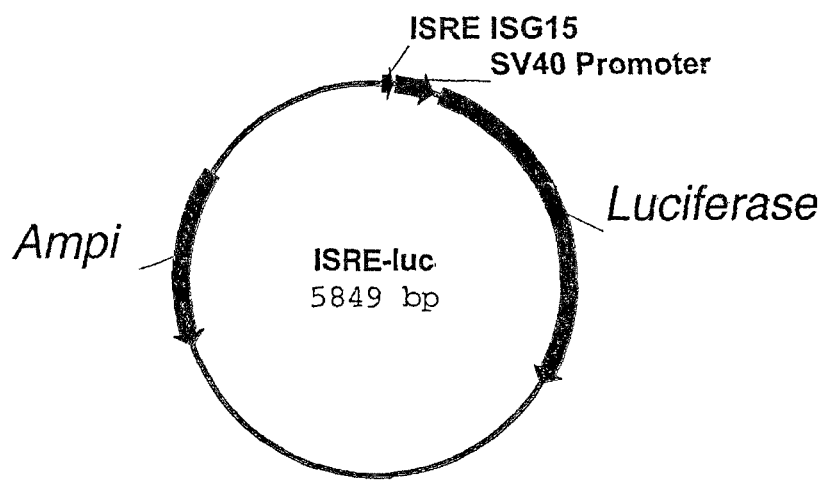
FIG. 1 shows a schematic representation of a luciferase reporter gene construct where luciferase expression is under the control of a chimeric promoter containing an interferon sensitive response element (ISRE) from the ISG15 gene and a minimal SV40 promoter.

The present invention is directed to an improved method for conducting an assay for the determination of the neutralization titer of antibodies in a sample where the antibodies are specific for (recognize and bind to) a predetermined target molecule that activates the signal transduction activity of a cell surface protein or a pattern recognition receptor and blocks the ability of the predetermined target molecule to activate the signal transduction activity of the cell surface protein or a pattern recognition receptor. The present invention is thus also directed to an improved method for determination of the neutralizing titer of antibodies that recognize molecules or preparations, such as live or attenuated virus or bacterial vaccines, components of which interact with pattern recognition receptors including, but not limited to, Toll like receptors (TLR) cell surface or endosomal membrane receptors (Uematsu and Akira, 2007), or the retinoic acid-inducible gene 1 (GIG-I)-like cytosolic receptor proteins RIG-I, MDA5, and LGP2 (Yoneyama and Fujitia, 2007). In addition, the present method can be used for a determination of the titer of neutralizing antibodies to antagonists of the predetermined target molecule.

The method of the present invention involves preparing a serial dilution of the sample, which is preferably a sample taken from the blood (serum) of a mammalian subject, and adding to each dilution a fixed amount of the target molecule (and a fixed amount of an antagonist of the target molecule if neutralizing antibodies to the antagonist is to be determined), which amount corresponds to a predetermined unit of activity of the target molecule, and where the concentration of the target molecule is the same in each dilution. Each dilution is then subjected to a reporter gene assay, which involves measuring the level of reporter gene product upon contact of the dilution with a cell line transformed with a reporter gene construct, to determine the amount of residual activity (ability of any remaining target molecules not neutralized by antibodies or antagonists to activate the signal transduction activity of the cell surface protein or pattern recognition receptor) of the target molecule in that dilution and then determining the dilution at which the activity of the added target molecule is reduced by a predetermined factor, x, where the neutralizing titer of antibodies is expressed as an x-fold reduction in units of activity/ml. This predetermined factor x is preferably 10, so that the titer of neutralizing antibodies is expressed as Ten-fold Reduction Units (TRU)/ml.

The improvement over standard conventional neutralization assays is that the sensitivity of the neutralization assay is increased in the method according to the present invention due to the use of a cell line in the receptor gene assay that has been previously treated with an anti-mitotic or pro-apoptotic agent so as to acquire the property that the cell line will maintain the signal transduction activity for at least about one hour, more preferably at least about eight hours, most preferably at least about eighteen hours, but will lose the signal transduction activity and undergo cellular death (apoptosis) in no more than about 30 days, preferably in no more than 14 days, more preferably in no more than 5 days or in no more than 24 hours, at a temperature above freezing.

The present inventors unexpectedly discovered that PIL5 cells (human promonocytic U937 cells transfected with the reporter gene construct of the luciferase reporter-gene controlled by an IFN responsive chimeric promoter; Lallemand et al., 1996) treated with an anti-mitotic or pro-apoptotic agent (i.e., vinblastin), so as to acquire the property that it will maintain the signal transduction activity for a period of time sufficient to conduct the neutralization assay but will lose the signal transduction activity and undergo cellular death in no more than 30 days at a temperature above freezing, actually behave better with improved sensitivity in neutralization assay than the corresponding untreated cells. As the "treated"

cells are not capable of replication, they are not considered "living" cells like the untreated PIL5 cells.

The cell line used in the method according to the present invention, of which the PIL5 cell line is a preferred embodiment, was previously disclosed in WO 2004/039990 and US 2004/0235157, both of which are incorporated herein by reference. The cell line disclosed in WO 2004/039990 and US 2004/0235157 is transformed with a reporter gene construct comprising a nucleotide sequence encoding a reporter gene product operatively linked to one or more transcriptional control elements that is regulated by the signal transduction activity of a cell surface protein in response to an extracellular signal (i.e., generated by the target molecule in the method according to the present invention). This cell has been treated in such a way that it will maintain the signal transduction activity of the cell surface protein for at least about 1 hour but no more than about 30 days at a temperature above freezing before losing the signal transduction activity. Not only does the cell have a sufficient shelf life by inhibiting cell division or by maintaining the cell in a frozen state for the purpose desired by an end user, such as for conducting an assay, but it has been treated in such a manner that the cells can be frozen, allowing storage for extended periods and transportation in a frozen state. Thus, the cell also has the commercial advantage to a supplier of being a one time use cell that cannot be propagated by the end user for possible further use. Instead, the cell, preferably as part of a kit, must be purchased from the supplier for each single use.

When comparing the reporter gene activity of "treated" cells and "living" cells against different titers of interferon (i.e., Example 2 hereinbelow), it can be seen that there is a substantially greater fold increase in reporter gene activity at lower titers of interferon for the treated cells as compared to the living cells. On the other hand, the living cells show greater responsiveness at higher interferon titers. Thus, treated cells exhibit a lower limit of interferon detection and improved interferon sensitivity. Sensitivity is defined as the mid-point of the interferon dose-response curve determined by the difference between the value obtained for the control sample without interferon and the value obtained for saturating doses of interferon.

The significance of this improved activity at lower interferon titers is that the treated cells are vastly superior to living cells in the quantitation of neutralizing antibodies against interferon. This is particularly apparent for potent anti-sera where consistently higher neutralizing titers are obtained using treated cells than live cells. The standard World Health Organization (WHO) approved methodology (Kawade et al., 1984; Grossberg et al., 2001a, b) for determining the presence of neutralizing antibodies in the serum, for example in the serum of patients having remitting/relapsing multiple sclerosis being treated by interferon β, is as follows. The assay determines the ability of serial dilutions of a patient's serum to reduce ten laboratory activity units to one laboratory activity unit, which is considered to be the end point. The neutralizing antibody titer is expressed as Ten-fold Reduction in Units per ml (TRU/ml).

Neutralizing antibody assays are clinically very important today because those patients being treated continuously for a chronic disease, such as remitting/relapsing MS treated with interferon β, cease obtaining benefit from treatment with the therapeutic agent once an immune response has been mounted against the therapeutic agent by the patient. Thus, it is important to be able to detect when and if a patient has developed such an immune response in order to stop treatment at that point. Also, it will prevent the possibility of adverse reactions such as anaphylactic shock and perfusion reactions.

There are two advantages to the improved sensitivity to lower interferon titers. First, there is the improvement whereby the lower limit of detection is reduced. By reducing the lower level of detection, one can detect smaller amounts of interferon in the assay, which may be important for various purposes.

The second advantage that is inherent in the neutralization assay method of the present invention is that the results will be significantly more accurate and more sensitive, particularly for patients with high levels of circulating anti-interferon antibodies. In the World Health Organization (WHO) approved neutralization assay, a single laboratory unit is determined as being the midpoint between the maximum reporter gene response and the minimum reporter gene response. At high interferon titers, the response levels off. It can be seen from the experimental results and figures in Example 2 hereinbelow that a significantly greater amount of interferon, nearly a power of 10 greater is necessary to provide one laboratory unit of activity when using living cells as opposed to treated cells. Because the curve for the treated cells is shifted significantly to the left, a much smaller amount of interferon is necessary to provide a single laboratory unit. Of course, it then follows that ten laboratory units will also be a power of 10 smaller titer of interferon in the treated cells as compared to the living cells. Because much smaller amounts of antibody are being neutralized in the assay, smaller amounts of antibody are necessary for neutralization and a more accurate determination of the amount of antibody that is necessary to neutralize 90% of that interferon can be made, thereby resulting in a much more accurate determination of antibody titer particularly at high antibody titers.

The sample which is assayed in the method according to the present invention is a biological fluid of a mammalian subject, preferably a human subject, in which antibodies are present, such as blood. Most preferably the sample is serum.

The cell line used in the present method may be any mammalian or avian cell line, with human cells most preferred. Preferred cell lines include but are not limited to, human promonocytic (i.e., U937), myeloid (i.e., U266R), T-cell lymphoma (i.e., Jurkatt), breast adenocarcinoma (i.e., MCF7) cell lines and mouse lymphoma (i.e., L120) and erythroid leukemia cell lines.

The predetermined target molecule (or its antagonist), for which the titer of neutralizing antibodies thereto are determined in the method according to the present invention, is intended to encompass any therapeutic agent, such as therapeutic proteins, which activates (or blocks, in the case of an antagonist of the target molecule) the signal transduction activity of a cell surface protein, and for which neutralizing antibodies generated thereto in the mammalian subject treated with the therapeutic agent would be undesirable. The predetermined target molecule may also encompass components of molecules or preparations such as live or attenuated virus or bacterial vaccines, which components interact with pattern recognition receptors. Preferred non-limiting examples of such a target molecule include interferon-α, interferon-β, interferon-γ, erythropoietin (EPO), TNFα, interleukins, growth hormone, gonadotropins, insulin and other hormones, granulocyte colony stimulating factor (G-CSF), and granulocyte macrophage colony stimulating factor (GM-CSF). Non-limiting examples of antagonists of the predetermined target molecule, which antagonist the neutralizing antibodies bind to, include TNFα antagonists such as Infliximab (a chimeric antibody), Adalimumab (a fully human antibody), and Etanercept (an IgG1Fc TNFp75 receptor fusion protein).

The cell surface protein from which its signal transduction activity, in response to an extracellular signal from a therapeutic agent or protein, regulates the expression of a reporter gene product can be any such cell surface protein that is known to those of skill in the art or that may be identified by those of skill in the art. Exemplary cell surface proteins include, but are not limited to, cell surface receptors and ion channels. Non-limiting examples of cell surface receptors include cytokine receptors (e.g., receptors for Type I interferon, Type II interferon, interleukins, growth hormone, erythropoietin (EPO), granulocyte colony stimulating factor (G-CSF), granulocyte macrophage colony stimulating factor (GM-CSF), TNFα, TGFβ, Fas ligand, leukemia inhibitory factor (LIF), ciliary neurotrophic factor (CNTF), etc.), growth factor receptors, hormone receptors, T cell receptors, antigen receptors, complement receptors, and neuroreceptors. The reference text, J. M. Cruse and Robert E. Lewis, *Atlas of Immunology*, CRC Press, Washington, D.C., 1999, which discloses many receptors involved in immune response and immune system interactions is entirely incorporated herein by reference. Cell surface receptors also include, but are not limited to, muscarinic receptors (e.g., human M2 (GenBank accession #M16404); rat M3 (GenBank accession #M16407); human M4 (GenBank accession #M16405); human M5 (Bonner et al., 1988); and the like); neuronal nicotinic acetylcholine receptors (e.g., the α2, α3 and β2 subtypes); the rat α2 subunit (Wada et al., 1988); the rat α3 subunit (Boulter et al., 1986); the rat α4 subunit (Goldman et al., 1987); the rat α5 subunit (Boulter et al., 1990); the rat β2 subunit (Deneris et al., 1988); the rat β3 subunit (Deneris et al., 1989); the rat β4 subunit (Duvoisin et al., 1989); combinations of the rat α subunits, β subunits and α and β subunits; GABA receptors (e.g., the bovine α1 and β1 subunits (Schofield et al., 1987); the bovine α2 and α3 subunits (Levitan et al., 1988); the γ-subunit (Pritchett et al., 1989); the β2 and β3 subunits (Ymer et al., 1989); the δ subunit (Shivers, B. D., 1989); and the like); glutamate receptors (e.g., receptor isolated from rat brain (Hollmann et al., 1989); and the like); adrenergic receptors (e.g., human β1 (Frielle et al., 1987); human α2 (Kobilka et al., 1987); hamster β2 (Dixon et al., 1986); and the like); dopamine receptors (e.g., human D2 (Stormann et al., 1990); rat (Bunzow et al., 1988); and the like); NGF receptors (e.g., human NGF receptors (Johnson et al., 1986); and the like); serotonin receptors (e.g., human 5HT1a (Kobilka et al., 1987); rat 5HT2 (Julius et al., 1990); rat 5HT1c (Julius et al., 1988); and the like).

The pattern recognition receptor from which its signal transduction activity, in response to an extracellular signal from a component(s) of a molecule or preparation such as a live or attenuated virus or bacterial vaccine regulates the expression of a reporter gene product, includes but is not limited to Toll-like receptors (TLR) cell surface or endosomal membrane receptors (Uematsu and Akira, 2007), or the retinoic acid-inducible gene 1 (GIG-I)-like cytosolic receptor proteins RIG-I, MDA5, and LGP2 (Yoneyama and Fujita, 2007) that recognize or interact with components of live or attenuated virus or bacterial vaccines. Evaluation of neutralizing antibodies generated in the mammalian subject treated with the vaccine is important in order to determine the degree of protection afforded by vaccination.

Thirteen members of the TLR family have been identified in mammals (Uematsu and Akira, 2007). Each TLR mediates a distinctive response in association with different combinations of four Toll/IL-1 receptor (TIR) domain-containing adaptor proteins (MyD88, TRIF, TIRAP/MAL, and TRAM). All the TLRs except TLR3 interact with MyD88. TLR3, which recognizes single-stranded or double-stranded viral RNA, is localized in the endosomes of myeloid DCs and requires acidification of vesicles for activation. TLR3 signals via TRIF and activates TBK1/IKKε which phosphorylates the interferon regulatory factor 3 (IRF3) and NFκB, resulting in production of IFN β (Hemmi et al, 2004, Perry et al., 2004). The RIG-1-like receptor proteins are DExD/H box RNA helicases two of which, RIG-I and MDA5, carry caspase activation.

Ion channels include, but are not limited to, calcium ion channels (e.g., human neuronal α2 subunit (see WO89/09834); rabbit skeletal muscle α1 subunit (Tanabe et al. 1987); rabbit skeletal muscle α2 subunit (Ellis et al., 1988); rabbit skeletal muscle β subunit (Ruth et al., 1989); rabbit skeletal muscle γ subunit (Jay et al., 1990); and the like); potassium ion channels (e.g., rat brain (BK2) (McKinnon, D., 1989); mouse brain (BK1) (Tempel et al., 1988); and the like); sodium ion channels (e.g., rat brain I and II (Noda et al., 1986); rat brain III (Kayano et al., 1988); and others).

It will be appreciated by those of skill in the art that the cell surface protein or pattern recognition receptor discussed above is preferably endogenous to the cell of the present invention. However, it will also be appreciated that the cell surface protein or pattern recognition receptor may be expressed from cloned DNA, such as to supplement the number of pattern recognition receptors or the number of the cell surface protein at the surface of the cell, or the cell surface protein or pattern recognition receptor may be expressed from cloned DNA but is a cell surface protein or pattern recognition receptor that is heterologous to the host cell.

For signal transduction, the intracellular signal that is transduced is initiated by the specific interaction of an extracellular signal, i.e., a molecule or a change in environment, with a receptor or ion channel present on the cell surface. This interaction sets in motion a cascade of intracellular events, the ultimate consequence of which is a rapid and detectable change in the expression of a gene product, which in the cell of the present invention is a reporter gene product. The extracellular signal or effector molecule is any compound or substance that in some manner specifically alters the activity of a cell surface protein or pattern recognition receptor. Examples of such signals include, but are not limited to, molecules such as cytokines (i.e., interferons), growth factors, hormones, endorphins, neurotransmitters, acetylcholine, and mitogenic substances, such as phorbol mistric acetate (PMA), that bind to cell surface receptors and ion channels and modulate the activity of such receptors and channels. Other examples include components of live and attenuated virus and bacterial vaccines.

The reporter gene construct carried by the cell used in the method according to the present invention is a DNA molecule that includes a nucleotide sequence encoding a reporter gene product operatively linked to transcriptional control elements/sequences. Transcription of the reporter gene is controlled by these sequences. The activity of at least one or more of these control sequences is directly or indirectly regulated by the cell surface protein or pattern recognition receptor. The transcriptional control sequences include but are not limited to promoters and other regulatory regions, such as enhancer sequences and repressor and activator binding sites, that modulate the activity of the promoter, or control sequences that modulate the activity or efficiency of the RNA polymerase that recognizes the promoter, or control sequences that are recognized by effector molecules, including those that are specifically induced by interaction of an extracellular signal with a cell surface protein or a pattern recognition receptor. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product expressed.

A promoter that is regulated or mediated by the activity of a cell surface protein or pattern recognition receptor is a promoter whose activity changes when a cell is exposed to a particular extracellular signal by virtue of the presence of cell surface proteins or pattern recognition receptors whose activities are affected by the extracellular signal. For example, the c-fos promoter is specifically activated upon the specific interaction of certain extracellular signals, such as growth hormones, with a cell surface protein, such as a growth hormone receptor. In particular, the regulation of such promoters by the cell surface protein, though indirect, occurs within minutes of the interaction of the cell surface protein with the extracellular signal. As used herein, operative linkage refers to the linkage of a transcriptional control element, i.e., promoter, to a nucleotide coding sequence such that the transcriptional control element is properly positioned for its activity of binding RNA polymerase and initiating transcription of the nucleotide coding sequence. Thus, a nucleotide coding sequence in operative linkage with a promoter is downstream, with respect to the direction of transcription, from the promoter, is in the correct reading frame with respect to the transcription initiation site and is inserted in a manner such that transcription elongation proceeds through the nucleotide coding sequence.

Suitable transcriptional control elements may be obtained or derived from the transcriptional regulatory regions of genes whose expression is rapidly induced, generally within minutes, of contact between the cell surface protein or pattern recognition receptor and the effector protein that modulates the activity of the cell surface protein or pattern recognition receptor. Examples of such genes include, but are not limited to, the immediate early genes (Sheng et al., 1990), such as c-fos. Immediate early genes are genes that are rapidly induced upon binding of a ligand to a cell surface protein. The transcriptional control elements that are preferred for use in the reporter gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Suitable promoters and transcriptional control elements include, but are not limited to, the vasoactive intestinal peptide (VIP) gene promoter (cAMP responsive; Fink et al., 1988); the somatostatin gene promoter (cAMP responsive; Montminy et al., 1986); the proenkephalin promoter (responsive to cAMP, nicotinic agonists, and phorbol esters; Comb et al. 1986); the phosphoenolpyruvate carboxy-kinase gene promoter (cAMP responsive; Short et al., 1986); the NGFI-A gene promoter (responsive to NGF, cAMP, and serum; Changelian et al., 1989); the transcriptional control elements obtained or derived from the c-fos gene; and others that may be known to or prepared by those of skill in the art.

The c-fos proto oncogene is the cellular homologue of the transforming gene of FBJ osteosarcoma virus. It encodes a nuclear protein that is most likely involved in normal cellular growth and differentiation. Transcription of c-fos is transiently and rapidly activated by growth factors and by inducers of other cell surface proteins, including hormones, differentiation-specific agents, stress, mitogens and other known inducers of cell surface proteins. Activation is protein synthesis independent. The c-fos regulatory elements include a TATA box that is required for transcription initiation, two upstream elements for basal transcription, and an enhancer, which includes an element with dyad symmetry and which is required for induction by TPA, serum, EGF, and PMA. The 20 bp transcriptional enhancer element located between −317 and −298 bp upstream from the c-fos mRNA cap site, which is essential for serum induction in serum starved NIH 3T3 cells. One of the two upstream elements is located at −63 to −57 and it resembles the consensus sequence for cAMP regulation.

Transcriptional control elements, particularly as they relate to a preferred embodiment of the present invention where Type I and/or Type II interferon is the extracellular signal, are preferably an interferon stimulatory response element (ISRE) and/or a gamma activated sequence (GAS). There are a number of ISREs characterized from different human genes responsive to Type I interferon and a consensus sequence, ggr aaagwGAAActg (SEQ ID NO:6; capital letters denote core sequence; underlines denote high conservation), to which the STAT1/STAT2/IRF9 complex binds, was identified for ISRE (Levy et al., 1988). A preferred ISRE is from the human ISG15 gene and is presented as SEQ ID NO:5 where nucleotides 41-55 correspond to the consensus ISRE sequence. ISRE is also highly conserved among species. For example, a sequence present in the promoter region of the interferon inducible chicken Mx gene (Schumacher et al., 1994) is similar to that found in primates and conforms to the ISRE consensus sequence for mammalian interferon responsive genes including rodents and cows (see FIG. 2 of Perry et al., 1999).

Regarding GAS, to which the STAT1 homodimer binds in genes responsive to Type II interferon, a consensus sequence, nnnsanttccgGGAAntgnsn (SEQ ID NO:7; capital letters denote core sequence; underlines denote high conservation), from many selected binding sequences was identified (Horvath et al., 1995).

In the instance where Type I interferon and/or Type II interferon is the extracellular signal, a preferred combination of transcriptional control elements is an interferon responsive chimeric promoter in which an ISRE and/or GAS controls a SV40 minimal promoter operatively linked to a nucleotide sequence encoding a reporter gene product.

The reporter gene product, whose level is a measure of the presence and/or the level of a molecule that activates the signal transduction activity of a cell surface protein or pattern recognition receptor, may be RNA or protein, as long as it is readily detectable. For instance, firefly luciferase, Gaussia luciferase and Metridia luciferase, enhanced green fluorescent protein (EGFP) and jellyfish aequorin are most preferred embodiments of reporter gene products used according to the method of the present invention. In the case of the enzyme firefly luciferase (dewet et al., 1987) and jellyfish aequorin (Rider et al., 2003), the result of its enzymatic activity, light, is detected and measured using a luminometer, whereas in the case of EGFP, a fluorescence activated cell sorter or analyzer (FACS) can be used at an appropriate wavelength to detect and quantify the amount of EGFP expressed in a cell. The distribution curve of the amount of luciferase, aequorin or EGFP expressed in a sample of cells will be determined by the amount of ligand (within a given range) to which the cell is exposed. Non-limiting examples of other suitable reporter gene products include dsRED, chloramphenicol acetyl transferase (CAT) (Alton et al., 1979) other enzyme detection systems, such as ε-galactosidase, bacterial luciferase (Engebrecht et al., 1984 and Baldwin et al. 1984), alkaline phosphatase (Toh et al. 1989 and Hall et al. 1983), and bacterial or humanized β-lactamase (Zlokarnik et al., 1998).

In order to provide the cell line used in the method according to the present invention, which is a one time use cell that cannot be propagated for further use, the cell transformed with a reporter gene construct is treated with an anti-mitotic or pro-apoptotic agent so as to acquire the property that it will maintain the signal transduction activity of the cell surface protein for at least about 1 hour but no more than about 30 days at a temperature above freezing before losing the signal transduction activity and undergoing cellular death.

One preferred embodiment of the present invention is where the anti-mitotic or pro-apoptotic agent is γ-radiation and the transformed cell is treated by irradiating with γ-radiation at an intensity and for a sufficient time such the irradiated cell maintains the signal transduction activity of the cell surface protein for a period of at least about 1 hour, preferably 7 days but no more than 30 days at a temperature above freezing following irradiation, after which period of time the irradiated cell immediately undergoes cellular death (i.e., apoptosis).

It is known that γ-irradiation at a high dose causes a cell to lose its signal transduction activity. Irradiation at a somewhat lower dose causes a cell to cease replication and undergo cellular death. The present inventors previously discovered that it is possible to determine a dose which inhibits replication but still allows a cell to maintains its signal transduction activity for a period of time before undergoing cell death. For example, γ-irradiation at about 9 Grays allows U937 cells to retain signal transduction activity for 14 days, after which the cells undergo cell death. However, during those 14 days, the signal transduction activity in response to, for example, Type I interferon that is being assayed functions as well as in a non-irradiated control. Thus, by irradiating a cell with γ radiation, the treated cell has a 14-day shelf life, but which becomes inactive (undergoes cellular death) after a period of about 14 days so that it cannot be maintained and reproduced by an end user. The dose of γ-irradiation required will vary as a function of the particular cell line employed but this can be determined with only routine experimentation based on the guidance in WO 2004/039990 and US 2004/0235157.

The dose (intensity and duration) of γ radiation to which the transformed cell is treated is preferably about 6 to 12 Grays (Gy). As the experiments in WO 2004/039990 and US 2004/0235157 demonstrate, the temperature above freezing, at which the cell is kept or stored, affects the shelf-life of the cell. Preferably, this temperature is room temperature, which advantageously maintains maximum interferon sensitivity while providing for ease of storage and shipping of the commercial one time use cell.

A second preferred embodiment of the present invention is where the transformed cell is treated with an anti-mitotic or pro-apoptotic chemical agent such as vinblastin, 5-fluorouracil (5-Fu), cisplatin or an anti-tumor intercalating agent (i.e., mitomycin C) in a sufficient amount and for a sufficient time such that the treated cell maintains the signal transduction activity of the cell surface protein or pattern recognition receptor for a period of at least about 1 hour but no more than about 30 days at a temperature above freezing following treatment with the agent, after which period of time the treated cell immediately undergoes cellular death. An anti-mitotic or pro-apoptotic agent will affect a treated cell when it begins to replicate, such as for example by preventing spindle formation, thereby inducing apoptosis and killing the cell. Thus, cells which have been treated with an anti-mitotic or pro-apoptotic agent, such as the human promonocytic cells transformed with a luciferase reporter gene construct, will have a shelf life of about 24 hours during which the signal transduction assay can be conducted and after which period of time the cells will die. It will be appreciated that a cell having only a 24 hour shelf life is not desirable from a commercial standpoint. In order to extend the shelf life, the treated cells may be immediately frozen, in which state they will have a much longer shelf life, depending upon the manner of freezing and thawing. Once thawed, however, they must be used within 24 hours, after which they will undergo cellular death (i.e., apoptosis).

It should be understood that conventional wisdom is that cryopreservation of cells requires a special freezing and thawing process (and equipment) in which the cells are frozen at a rate of 1° C. per minute until it reaches −80° C. or liquid nitrogen temperatures of about −200° C., where it may be stored indefinitely, and after which it must be thawed very rapidly. Often, dimethyl sulfoxide (DMSO) or another cryopreservative is also used in order to help protect the cells. As most laboratories do not have storage facilities at −200° C. or even −80° C., it would be useful to allow freezing of the cells to occur at −20° C. However, it is known that cell viability is poor when cells are frozen at −20° C. and then thawed. It was previously found by the present inventors that DMSO will protect the cells even when frozen at −20° C. without any special freezing or thawing techniques or equipment. While glycerol, a known cryopreservative compound, will protect cells at −20° C., there is the possibility that it may prevent protein ligands from interacting with surface receptors at the high percentage (50%) of glycerol conventionally used for cryopresevation. However, a low percentage of glycerol (much less than the 50% conventionally used) can be used. DMSO does not have this disadvantage. DMSO can thus protect cells frozen at −20° C. without any special freezing or thawing techniques or equipment being required and without adversely affecting their sensitivity to IFN. After treating with an anti-mitotic and pro-apoptotic agent, a cell may achieve a long shelf life even at standard freezer temperatures of −20° C. if further treated with DMSO and that once thawed such a cell will remain active, i.e., for signal transduction assays, for approximately 24 hours until it undergoes apoptosis as a result of being treated with an anti-mitotic and pro-apoptotic agent. Any anti-mitotic, or pro-apoptotic agent which kills cells during the process of replication by inducing apoptosis, such as γ-radiation and chemical agents such as vinbastin, 5-FU, cisplatin, or an anti-tumor intercalating agent (i.e., mitomycin C) can be used for this purpose as it would be expected that the cells will remain biologically active during a quiescent period and until such time the treated cells start to die.

The treated transformed cell is frozen at a temperature and under conditions such that it will resume signal transduction after thawing. While the cell is preferably frozen at a temperature between −20° C. and −200° C., more preferably at −80° C., cells may be subsequently stored at −20° C., a commonly available freezer temperature in almost all laboratories, it is intended that other suitable temperatures for cryopreservation of cells, such as the liquid nitrogen temperature of about −200° C., be encompassed. It is further preferred that the treated transformed cell be resuspended in a solution containing a cryopreservative before freezing the cell. Dimethyl sulfoxide (DMSO) is the preferred cryopreservative although other suitable cryopreservatives which have a high bonding affinity to water, such as ethylene glycol, polyethylene glycol, propylene glycol, glycerol, butane diol, propanediol, and formamide, may be used so long as they do not interfere with the use of the cell after thawing. When DMSO is used alone as the cryopreservative, the solution containing DMSO preferably contains about 10% DMSO. More preferably, 2.5% DMSO is used in combination with 10% glycerol as the cryopreservative.

Figure 2:
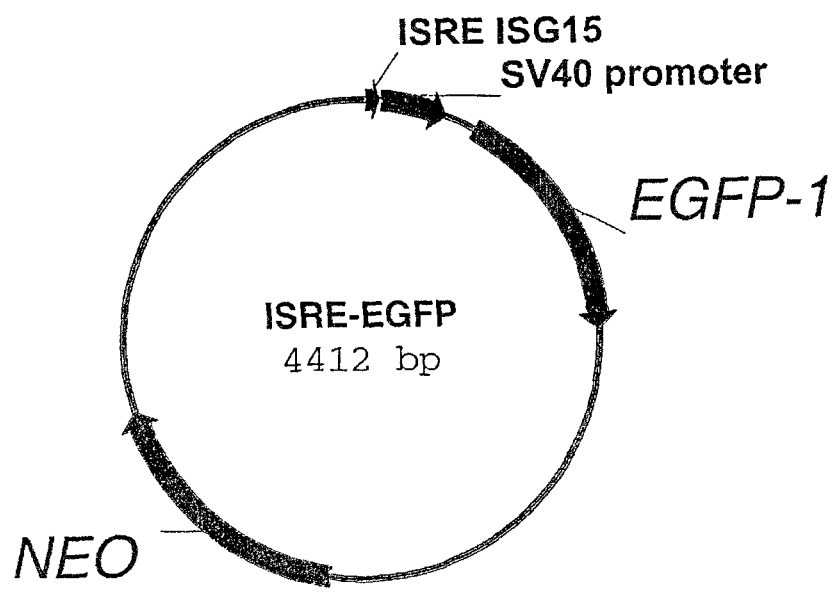
FIG. 2 shows a schematic representation of an enhanced green fluorescent protein (EGFP-1) reporter gene construct where EGFP-1 expression is under the control of a chimeric promoter containing an ISRE from the ISG15 gene and a minimal SV40 promoter.

The method of the present invention which uses a gene reporter assay for Type I interferon to determine the titer of neutralizing antibodies for Type I interferon is a most preferred embodiment of the present invention. The reporter gene product is preferably firefly luciferase, jellyfish aequorin, or enhanced green fluorescent protein (EGFP) and is preferably under the control of an interferon sensitive chimeric promoter containing the ISRE from ISG15 and a minimal SV40 promoter. Examples of such reporter gene constructs are presented in FIGS. 1 and 2. FIG. 1 is a schematic representation of a luciferase gene reporter construct in an ISRE-luc vector (SEQ ID NO:1), where the ISRE from ISG15 (SEQ ID NO:5) is positioned at nucleotides 38-97 of SEQ ID NO:1, the SV40 minimal promoter is positioned at nucleotides 103-288 of SEQ ID NO:1, and the coding sequence of the luciferase reporter gene having the amino acid sequence of SEQ ID NO:2 is positioned at nucleotides 328-1980 of SEQ ID NO:1. Similarly, FIG. 2 is a schematic representation of a EGFP gene reporter construct in an ISRE-EGFP vector (SEQ ID NO:3), where the ISRE from ISG15 is positioned at nucleotides 30-89 of SEQ ID NO:3, the SV40 minimal promoter is positioned at nucleotides 95-290 of SEQ ID NO:3, and the coding sequence of the EGFP reporter gene having the amino acid sequence of SEQ ID NO:4 is positioned at nucleotides 358-1077 of SEQ ID NO:3.

As for the cell used in the preferred gene reporter assay for Type I interferon embodiment of the present invention, the cell is preferably a mammalian or avian cell, more preferably a human cell, and most preferably a human promonocytic cell. A preferred human promonocytic cell carrying the ISRE-luc vector containing the luciferase gene reporter construct is a PIL5 cell. Other preferred cell lines include, but are not limited to, human myeloid (i.e., U266R), human T-cell lymphoma (i.e., Jurkatt), human breast adenocarcinoma (i.e., MCF7) cell lines and mouse lymphoma (i.e., L1210) and mouse erythroid leukemia cell lines. The cell is treated to make a commercial cell line that has the commercially desirable properties of a sufficient shelf life for the purpose of the assay and of being a one time use cell that cannot be propagated for possible further use. Preferably, the cell is treated either 1) by irradiating with 6 to 12 Gy of γ radiation, more preferably about 9 Gy, and storage at room temperature for up to 14 days after irradiation or 2) by exposure to an anti-mitotic and pro-apoptotic agent, such as vinblastin, cisplatin, or 5-fluorouracil, most preferably vinblastin, for 10 minutes at 37° C. prior to resuspending in a solution containing 40% fetal bovine serum (FBS) and 2.5% DMSO+10% glycerol and freezing at −80° C.

In order to optimize the method of obtaining a cell with an indefinite shelf life during frozen storage, but which will die approximately 24 hours after being thawed (once thawed, however, the product has excellent sensitivity, and precision as well as selectivity), the parameters which can be varied in the course of such optimization include:

1) Concentration of FBS. Besides FBS, most any serum could be used as it acts as a toxic sink to protect the cells from toxins, such as while being thawed or while being treated with an anti-mitotic and pro-apoptotic agent. The concentration of FBS can cause the results to vary.

2) Time is a variable. The amount of time of exposure to an anti-mitotic and pro-apoptotic chemical agent, such as vinblastin, before the cells are centrifuged out and washed to remove the agent (i.e., vinblastin).

3) Using vinblastin as a non-limiting example, the formulation of the vinblastin makes a difference. Presently, soluble vinblastin in a proprietary prebuffered formulation sold by Eli Lilly under the name Velbe in France is preferably used. A different formulation may require slightly different combination of parameters.

4) The concentration of vinblastin.

5) Cell concentration during the vinblastin treatment.

6) The amount of cryopreservative or combination of cryopreservatives.

All of these parameters can be varied empirically and the results after freezing tested for sensitivity and precision, assuming that the cells stay alive for approximately 24 hours after being thawed. This can be readily determined by one of ordinary skill in the art without undue experimentation, particularly in view of the guidance provided in the experiments shown in FIGS. 11-24 for PIL5 cells in WO 2004/039990 and US 2004/0235157, in order to arrive at a product having substantially the same sensitivity as the untreated live cells for a period of at least one hour, preferably 8-24 hours, following thawing but having a viability of no more than 30 days, preferably no more than 14 days, more preferably no more than 5 days, most preferably no more than 3 days.

Exemplified below are protocols for preparation of microtiter assay plates and ampoules/vials of PIL5 cells (as model cells) treated with the anti-mitotic and pro-apoptotic agent 1 Mg/ml vinblastin for 10 minutes at 37° C. prior to frozen storage at −20° C. and thawing at a later time for purposes of conducting the assay.

Preparation of Microtiter Assay Plates

1. PIL5 cells at a concentration of about $2\times10^5$ to $7\times10^5$ cells/ml in RMPI 1640 medium with 10% fetal bovine serum (FBS) are treated with a fresh solution of 1 μg/ml vinblastin (commercially available from Eli Lilly under the pre-buffered formulation VELBE), diluted from 1 mg/ml in $H_2O$, for 10 minutes at 37° C. in an atmosphere of 5% $CO_2$ in air. A $CO_2$ incubator can be used for convenience.

2. The PIL5 cells are centrifuged at 800×g for 10 minutes at 4° C., and washed once with the same volume of RPMI 1640 medium with 10% FBS to remove the vinblastin.

3. The PIL5 cells are re-suspended at a concentration of $2\times10^7$ cells/ml in RMPI 1640 medium with 40% fetal bovine serum (FBS) and 2.5% dimethylsulfoxide +10% glycerol.

4. The cell suspension is dispensed into the wells of a flat-bottom micro-plate to give 300,000 cells per well (equivalent to 25 μl of cell suspension per well).

5. The micro-plate is frozen at −80° C. in an aluminum bag sealed under vacuum with the cover uppermost.

6. The micro-plates can be subsequently stored for limited periods at −20° C. until use.

Alternatively, PIL5 cells at a concentration of $2\times10^7$ cells/ml in RMPI 1640 medium with 40% fetal bovine serum (FBS) and 2.5% dimethylsulfoxide +10% glycerol can be frozen in a single or multiple cryopreservation viales. Immediately prior to use the viale is thawed rapidly and the cells distributed into one or more microtiter plates. Viales may also be prepared containing sufficient cells for half or a quarter of a microtiter plate as required.

Preparation of Cryopreservation Ampoules/Vials

1. PILS cells at a concentration of about $2 \times 10^5$ to $7 \times 10^5$ cells/ml in RMPI 1640 medium with 10% fetal bovine serum (FBS) are treated with a fresh solution of 1 μg/ml vinblastin (commercially available from Eli Lilly under the prebuffered formulation VELBE), diluted from 1 mg/ml in $H_2O$ for 10 minutes at 37° C. in an atmosphere of 5% $CO_2$ in air. A $CO_2$ incubator can be used for convenience.

2. The PILS cells are centrifuged at 80×g for 10 minutes at 4° C., and washed once with the same volume of RPMI 1640 medium with 10% FBS to remove the vinblastin.

3. The PILS cells are re-suspended at a concentration of $2 \times 10^7$ cells/ml in RMPI 1640 medium with 40% fetal bovine serum (FBS) and 2.5% dimethylsulfoxide +10% glycerol.

4. The cell suspension (1 ml) is dispensed into a cryopreservation vial and frozen at −80%.

5. The cryopreservation vial can be subsequently stored at −20° C. until use.

The materials and methods for conducting the luciferase gene reporter assay for Type I interferon and the neutralization assay for neutralizing antibodies to Type I interferons are presented in the Materials and Methods section of Example 2 hereinbelow.

Having now generally described the invention, the same will be more readily understood through reference to the following examples which are provided by way of illustration and is not intended to be limiting of the present invention.

Example 1

The disadvantages of quantifying interferons have been overcome by the recent development of a highly sensitive and reproducible method for quantifying IFN activity based on the establishment of a human cell line transfected with the luciferase reporter gene placed under the control of an IFN responsive chimeric promoter. This recent method allows IFN activity to be determined in a few hours rather than in the 3 to 4 days required for a bioassay. Briefly, the interferon stimulatory response element (ISRE) from the ISG15 gene controlling a SV40 minimal promoter was cloned upstream of the luciferase reporter gene in a 5849 bp ISRE-luc vector (FIG. 1; SEQ ID NO:1). Alternatively, the ISRE from the ISG15 gene controlling a SV40 minimal promoter is cloned upstream of an enhanced green florescent protein (EGFP-1) reporter gene in a 4412 bp ISRE-EGFP vector (FIG. 2; SEQ ID NO:3). Human promonocytic U937 cells were transfected with the IFN regulated gene reporter construct and stable transfectants were isolated and cloned. A human cell line PIL5 carrying the luciferase reporter gene under the control of an IFN responsive chimeric promoter was thus established and provides the basis of an assay which allows IFN activity to be determined more rapidly and with greater precision than the standard antiviral bioassay (Lallemand et al., 1996). Table 1 presents the advantages of the luciferase gene reporter assay for interferon using PIL5 cells over the standard antiviral bioassay and Table 2 presents a comparison between the luciferase gene reporter assay for interferon using PIL5 cells and the standard antiviral bioassay on sensitivity to interferon produced as a result of infection by various viruses.

TABLE 1

| Parameter | CPE | MxA ELISA | MxA PCR | Reporter-Gene Cell-line | Reporter-Gene iLite Kit |
|---|---|---|---|---|---|
| Duration | 3-4 days | 2-3 days | 2-3 days | 1-2 days | 7-16 hours |
| Containment | P3 | NA | NA | NA | NA |
| Analyst Expertise | Highly specialized | Cell culture + Assay | Cell culture + Assay | Cell culture + Assay | Assay only |
| Reagent Availability | Restricted | Antibody Limited | Q-PCR Instrument | Cell-line Limited | Readily Available |
| Sensitivity IU/ml | 1.0 | NA | NA | 10 | 1.0 |
| Minimum IFN Level Detectable (IU/ml) | 5.0 | NA | NA | 1.5 | 0.2 |
| Selectivity | Low | High | High | High | High |
| Assay Variation with Cell Culture | Yes | Yes | Yes | Yes | No |
| High Throughput | No | Moderate | Moderate | Yes | Yes |
| IP restrictions | NA | Yes | Yes | Yes | No |
| Transferability to CRO | Restricted | Restricted | Restricted | Restricted | Unrestricted |

TABLE 2

| | Sensitivity (IU/ml) | | Lower Limit of Detection (IU/ml) | |
|---|---|---|---|---|
| Interferon | Live Cells | Chemically Treated Cells | Live Cells | Chemically Treated Cells |
| IntronA ™ | 15 | 4.0 | 1.0 | 0.25 |
| Avonex ™ | 10 | 2.5 | 1.5 | 0.2 |
| Rebif ™ | 10 | 1.0 | 1.5 | 0.2 |
| Betaferon ™ | 10 | 3.0 | 2.0 | 0.5 |

The gene reporter assay using PIL5 cells is highly sensitive (less than 1.0 TU/ml of IFNα or IFNβ can be detected routinely), reproducible (standard error +/−10%), and can detect IFN activity over a wide range of concentrations (0.1 to 100 IU/ml). The assay method is also highly specific and can for example even detect low levels of Type I IFNs (IFNα or IFNβ) in the presence of high levels of IFNγ which is not possible using a conventional antiviral bioassay. The assay is ideally suited for the determination of IFN activity in biological fluids such as human serum, cerebrospinal fluid, or urine as the method is less subject to non-specific interference at low dilutions than the conventional anti-viral bioassay. Human serum and other biological fluids often contain non-specific inhibitors of virus-replication unrelated to IFN which can affect virus replication at low dilutions giving rise to false positives.

The PIL5 gene-reporter IFN assay recognizes any Type I interferon which binds to a Type I interferon receptor. It also provides a means of distinguishing between one IFNα subtype and another due to the ability to detect differences in the dose response (standard) curves characteristic of individual IFNα sub-types. This is of considerable value in distinguishing between interferons produced under different circumstances. Paramyxo viruses such as Sendai induce mainly IFNα1, IFNα2, and IFNβ, while type I interferon produced by certain cells in the apparent absence of viral infection consist mainly of IFNα5 (Lallemand et al., 1996). Standard curves of luciferase activity in PIL5 cells in the presence of different amounts of each of the various isotypes of interferon is presented in FIG. 3.

Thus, this method developed previously by the present inventors for the determination of IFN levels in biological fluids, which has been used to analyze numerous clinical samples from virus infected individuals, is rapid, inexpensive, robust, does not require specialized personnel or equipment, and is readily automated. The PIL5 gene-reporter assay is based, however, on the use of live cells which limits commercialization in its present form, due to a severely limited shelf life and the ability of a customer to retain and cultivate the PIL5 cell line thereby obviating the necessity to purchase further kits. The experiments presented in WO2004/039990 and US Patent Appl. Publ. 2004/0235157, which are incorporated herein by reference, were conducted to develop a modified form of the PIL5 gene reporter assay amenable to commercialization in a kit format, where the PIL5 cells are treated so as to have a sufficiently long shelf life as part of a commercial assay, and whereupon at the end of its useful shelf life or at the end of its use in a PIL5 gene reporter assay, the treated PIL5 cells undergo cellular death such as by apoptosis. The experimental approach adopted as described in WO2004/039990 and US Patent Appl. Publ. 2004/0235157, is based on the use of anti-mitotic or pro-apoptotic agents to prevent cell multiplication and to induce delayed cellular death (i.e., apoptosis) while retaining a functional IFN signal transduction pathway. Fractional doses of γ irradiation can also be used to prevent cell multiplication and to induce delayed cellular death while retaining a functional IFN signal transduction pathway as also shown in WO2004/039990 and US Patent Appl. Publ. 2004/0235157. The entire content of US Patent Appl. Publ. 2004/0235157 is hereby incorporated by reference.

Example 2

A highly sensitive and reproducible method for quantifying type I IFN activity has been developed, based on human pro-monocytic U937 cells, transfected with the luciferase reporter-gene controlled by an IFN responsive chimeric promoter (Lallemand et al., 1996), which allows IFN activity to be determined selectively with a high degree of precision, and within a few hours. Treatment of these cells (PIL5) with the anti-mitotic and pro-apoptotic drug vinblastin allows cells to be stored frozen for prolonged periods without loss of IFN sensitivity or the need for cell culture and obviates assay variation associated with cell proliferation. The use of this assay to determine neutralizing titer applying the Kawade method (Kawade et al., 1984), which calculates the serum dilution that reduces IFN activity from 10 to 1 Laboratory Units (LU)/ml (Grossberg et al., 2001a,b), has shown that neutralizing antibodies (NABs) detected in patients with chronic hepatitis C treated with ROFERON™ or INTRONA™ exhibited comparable NAB titers when assayed against either IFNα2a or IFNα2b but markedly lower titers against IFNα1 or pegylated IFNα2a (PEGASYS™), which have specific activities approximately ten fold lower than either IFNα2a or IFNα2b. Similarly, sera from patients with RRMS treated with IFN β-1a (AVONEX or REBIF) neutralize both types of IFN to the same extent but exhibit markedly lower neutralizing titers against IFNβ-1b (BETAFERON). When the same sera were tested using a constant quantity (50 or 250 pg) of IFN protein, similar neutralizing titers were obtained for all IFNα or IFNβ subtypes tested suggesting that neutralization titer is dependent upon the specific activity of the IFN subtype used in the neutralization assay.

Materials and Methods

Patient Sera

Sera from patients treated with recombinant IFN α, or recombinant IFN β, and monitored for the presence of neutralizing anti-IFN antibodies were randomly selected for evaluation in the present study.

Interferon Preparations

Recombinant IFNα2a (ROFERON-A™) was purchased from Hoffmann-La Roche, Neuilly-sur-Seine, France. The preparation used in this study had a titer of $9.0 \times 10^6$ IU/ml on human amnion WISH cells challenged with vesicular stomatitis virus (VSV). The preparation was standardized against the human IFNα international reference preparation (G-023-901-527). The specific activity of the interferon preparation was $2 \times 10^8$ IU/mg protein.

Pegylated IFNα2a (PEGASYS™), a 40 kDa branched monomethoxy PEG conjugate of IFN-α2a, was purchased from Hoffmann-La Roche, Neuilly-sur-Seine, France.

Recombinant IFNα2b (INTRON-A™) was purchased from Schering-Plough, Levallois-Perret, France. The preparation used in this study had a titer of $10 \times 10^6$ IU/ml on human WISH cells challenged with VSV. The preparation was standardized against the human IFNα international reference preparation (G-023-901-527). The specific activity of the interferon preparation was $2 \times 10^8$ IU/mg protein.

Pegylated IFNα2b (PEG-INTRON™), a 12 kDa linear monomethoxy PEG conjugate of IFNα2b, was purchased from Schering-Plough, Levallois-Perret, France.

Recombinant IFNβ-1a (AVONEX™) was purchased from Biogen, Nanterre, France. The preparation used in this study had a titer of $6 \times 10^6$ IU/ml on human WISH cells challenged with VSV. The preparation was standardized against the human IFN β international reference preparation (Gb23-902-531). The specific activity of the interferon preparation was $2 \times 10^8$ IU/mg protein.

Recombinant IFNβ-1b (REBIF™) was purchased from Serono, Boulogne, France. The preparation used in this study had a titer of $6 \times 10^6$ IU/ml on human WISH cells challenged with VSV. The preparation was standardized against the human IFNβ international reference preparation (Gb23-902-531). The specific activity of the interferon preparation was $2.7 \times 10^8$ IU/mg protein.

Recombinant IFNβ-1b (BETAFERON™) was purchased from Schering A G, Berlin, Germany. The preparation used in this study had a titer of $8 \times 10^6$ IU/ml on human WISH cells challenged with VSV. The preparation was standardized against the human IFNβ international reference preparation (Gxb02-901-535). The specific activity of the interferon preparation was $3.2 \times 10^7$ IU/mg protein.

Recombinant human IFNγ was purchased from PBL, Piscataway, N.J. The preparation used in this study had a titer of $1 \times 10^7$ IU/ml on human WISH cells challenged with VSV. The preparation was standardized against the human IFNγ international reference preparation (Gxg-902-535). The specific activity of the interferon preparation was $1.6 \times 10^7$ IU/mg protein.

Interferon Assays

IFN Bioassay. IFN activity was assayed by the inhibition of the cytopathic effect (CPE) of vesicular stomatitis virus (VSV) on the human amnion cell line WISH or human HuH7 cells as described previously (Tovey et al., 1977), or by the inhibition of the CPE of encephalomyocarditis virus (EMCV) on human A549 cells as described previously (Grossberg et al., 2001a).

PIL5 Gene-Reporter Assay. The synthetic double-stranded oligonucleotide CTCGGGAAAGGGAAACCGAAACT-GAAGCC (SEQ ID NO:8), corresponding to the IRSE from the ISG 15 gene, controlling a SV40 minimal promoter was cloned upstream of the luciferase reporter gene by insertion into the Xho/BglII site of the pGL2-promoter vector (Promega) to generate the IFN regulated gene reporter construct as previously described (Lallemand et al., 1996). Human promonocytic U937 cells were transfected with the IFN regulated gene reporter construct and stable transfectants were isolated and cloned. A human cell line, PIL5, carrying the luciferase reporter gene under the control of an IFN responsive chimeric promoter was thus established. PIL5 cells form the basis of an assay that allows type I IFN activity to be determined selectively, rapidly and with a high degree of precision. Assay-ready vinblastin-treated replication-arrested PIL5 cells (iLite Alpha-Beta assay) were obtained from NeutekBio, Galway Ireland, and stored frozen at −80° C. until use, according to the manufacturers instructions. Briefly, frozen cells were thawed rapidly and incubated overnight in a 96-well micro-titer plate (50,000 cells/well), in duplicate with serial dilutions of IFN. Cells were then lysed by the addition of the luciferase substrate containing reagent and luciferase activity was determined in a luminometer (LumiCount™, Packard Instruments Inc, Downers Grove Ill.). Interferon activity of samples was determined from the dose-response curve of relative luciferase units (RLU) against dilution of the international IFN reference preparation and expressed in IU/ml.

Neutralization Assay

Briefly, serial dilutions of human serum were incubated in duplicate for 1 hour at 37° C. followed by 2 hours at 4° C. with a constant quantity (10 LU/ml or 50 to 250 pg/ml) of a particular IFN preparation in RPMI 1640 medium +2% fetal bovine serum (FBS) in a 96-well micro-titer plate. Residual IFN activity was then assayed using either the IFN bioassay or the PIL5 gene-reporter assay. The IFN preparation used in the neutralization test was also assayed simultaneously to determine its precise IFN activity. The lowest dilution of serum tested was also assayed alone for the presence of IFN activity or toxicity.

Neutralizing titer was determined using the Kawade method of calculation (Kawade et al., 1984) which determines the reciprocal of the antibody dilution that reduces IFN activity from 10 to 1.0 LU/ml according to the formula; t=f (n−1)/9, where f=the reciprocal of the antibody dilution, and n=IFN concentration in LU/ml (Grossberg et al., 2001a,b). Thus, when n=10 LU/ml, t=f. Neutralizing titers are expressed as Tenfold Reduction Units/ml, or TRU/ml (Grossberg et al., 2001a,b). Neutralization titers were corrected for the actual number of LU/ml of IFN used in the neutralization assay from the value obtained in the simultaneous IFN titration. This neutralization assay, as recommended by the World Health Organization (WHO), is considered the conventionally accepted standard for a neutralization assay.

Results

Determination of Type I IFN Activity Using the iLite Gene-Reporter Assay

Figure 4A:
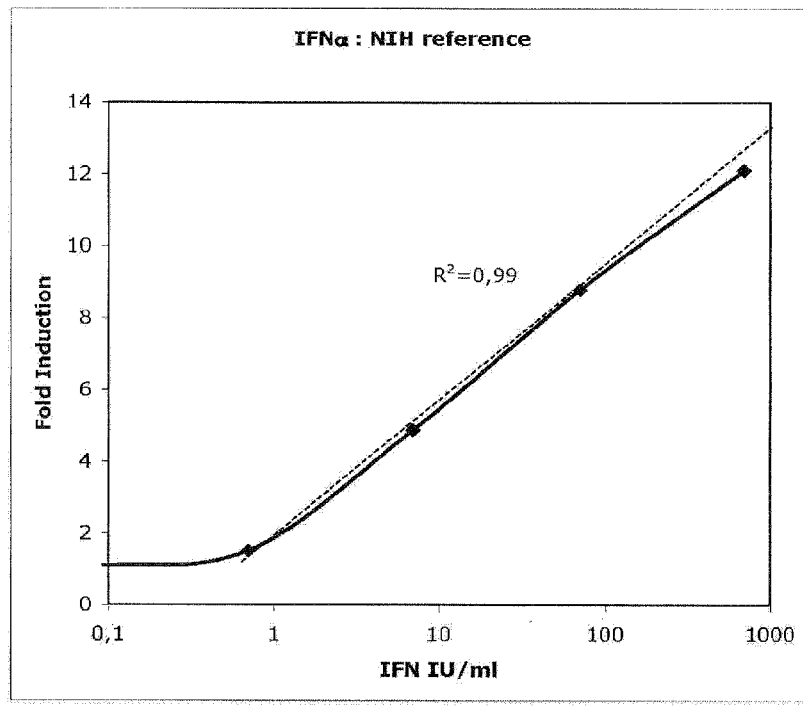
FIGS. 4A and 4B are graphs of dose-response curves for human type I interferons. Live PIL5 cells were incubated overnight with serial ten-fold dilutions of the human IFN alpha international reference preparation (G-023-901-527) as shown in FIG. 4A, or the human IFN beta international reference preparation (Gb23-902-531) as shown in FIG. 4B. Cells were then lysed with the luciferase substrate containing reagent and luciferase activity was determined using a luminometer as described in the Materials and Methods of Example 2. IFN activity was determined from the dose-response curve of relative luciferase units (RLU), expressed as fold induction, against IFN concentration expressed as IU/ml.
Figure 4B:
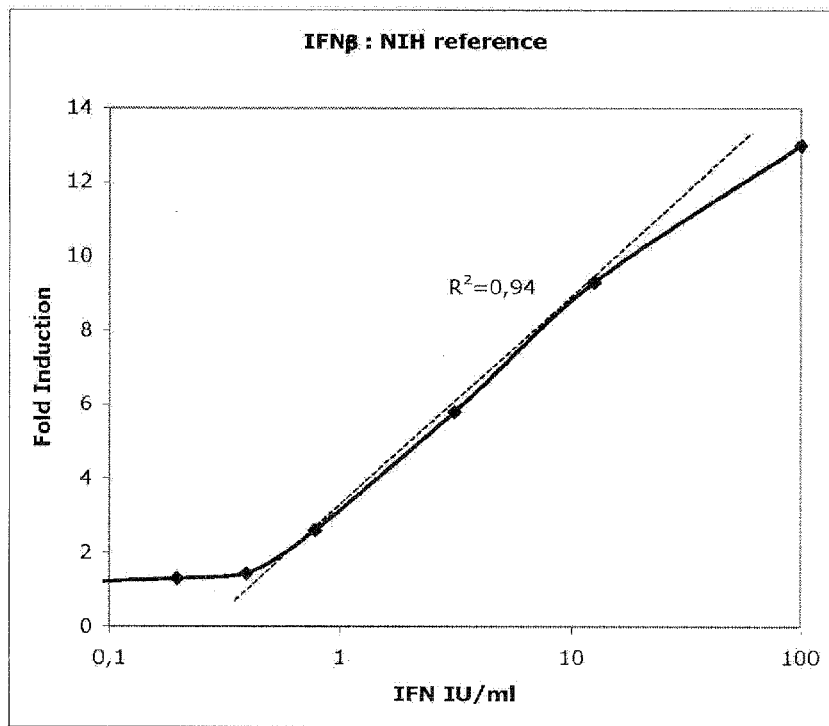

Human pro-monocytic U937 cells, were transfected with the luciferase reporter-gene controlled by an IFN responsive chimeric promoter as described in the Materials and Methods. Stable transfectants were isolated, cloned, and tested for IFN sensitivity. A cell-line, PIL5, was thus established which allows human type I IFN activity to be determined selectively with a high degree of precision, and within a few hours (FIGS. 4A and 4B). In order to obviate assay variation associated with the use of continuously cultivated cell-lines, master and working cell-banks were established and conserved in liquid nitrogen. For each batch of assay cells an ampoule of PIL5 cells was thawed and the cells were amplified for a constant number of passages under standardized conditions. Cells were then treated with the anti-mitotic drug vinblastin which allows assay-ready cells to be stored frozen at −80° C. for extended periods (>3 years) without loss of IFN sensitivity or the need for cell culture. This procedure obviates assay variation associated with cell proliferation.

Figure 3:
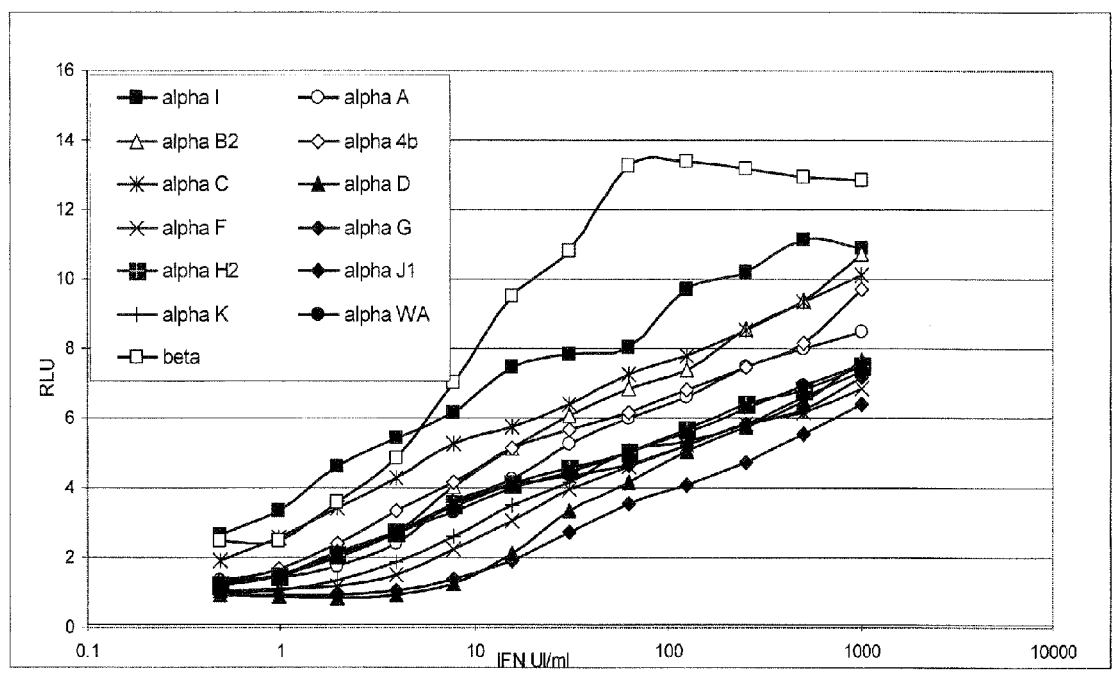
FIG. 3 is a graph of dose-response curves for human IFNα subtypes. Live frozen PIL5 cells were incubated overnight with serial ten-fold dilutions of one of the human IFN alpha subtypes or IFN β. Cells were then lysed with the luciferase substrate containing reagent and luciferase activity was determined using a luminometer as described in the Materials and Methods of Example 2. IFN activity was determined from the dose-response curve of relative luciferase units (RLU), expressed as fold induction, against IFN concentration expressed as IU/ml.

Vinblastin treated assay-ready frozen PIL5 cells (iLite Alpha Beta Assay, NeutekBio, Galway, Ireland) were used to determine the IFN activity of a number of well characterized IFN preparations. Briefly, frozen cells were thawed rapidly and incubated overnight with serial ten-fold dilutions of IFNα2a (ROFERON-A™), IFNα2b (INTRON-A™), pegylated IFNα2a (PEGASYS™), pegylated IFNα2b (PEG-INTRON™), IFNβ-1a (AVONEX), IFNβ1a (REBIF), IFNβ-1b (BETAFERON). Cells were then lysed with the luciferase substrate containing reagent, and luciferase activity was determined using a luminometer. Interferon activity was then determined from the dose-response curve of luciferase activity expressed in relative light units (RLU) against IFN concentration expressed in international units/ml (IU/ml) by calibration against the WHO international reference preparation for human IFNα or IFNβ. The iLite assay was capable of detecting 1.0 IU/ml or less of either IFNα or IFNβ with a standard error of +/−15%, over a wide range (<1.0 to 100 IU/ml) of IFN concentrations (FIGS. 4A and 4B). The iLite assay was also capable of detecting all the human IFNα sub-types tested (FIG. 3).

Figure 5A:
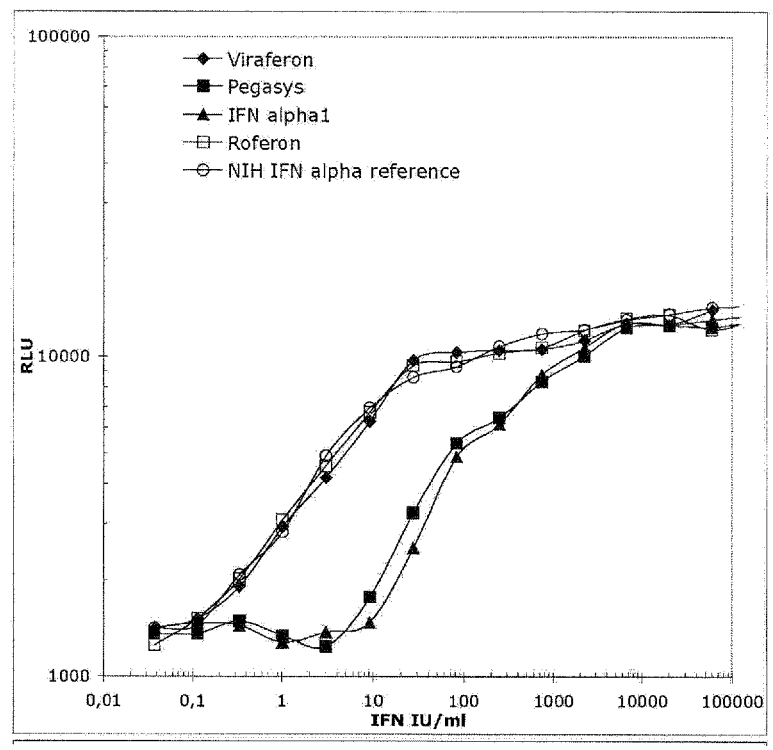
FIGS. 5A and 5B are graphs of dose-response curves for clinically formulated preparations human IFNα and IFNβ.

The specific activity of pegylated IFNα2a (PEGASYS™), determined using the iLite assay was found to be approximately ten fold lower than that of the native non pegylated IFNα2a (ROFERON-A™) as shown in FIG. 5A. In contrast the specific activity of pegylated IFNα2b (PEG-INTRON™), was found to be only slightly lower than that of native IFNα2b (INTRON-A™) as shown in FIG. 5A.

Figure 5B:
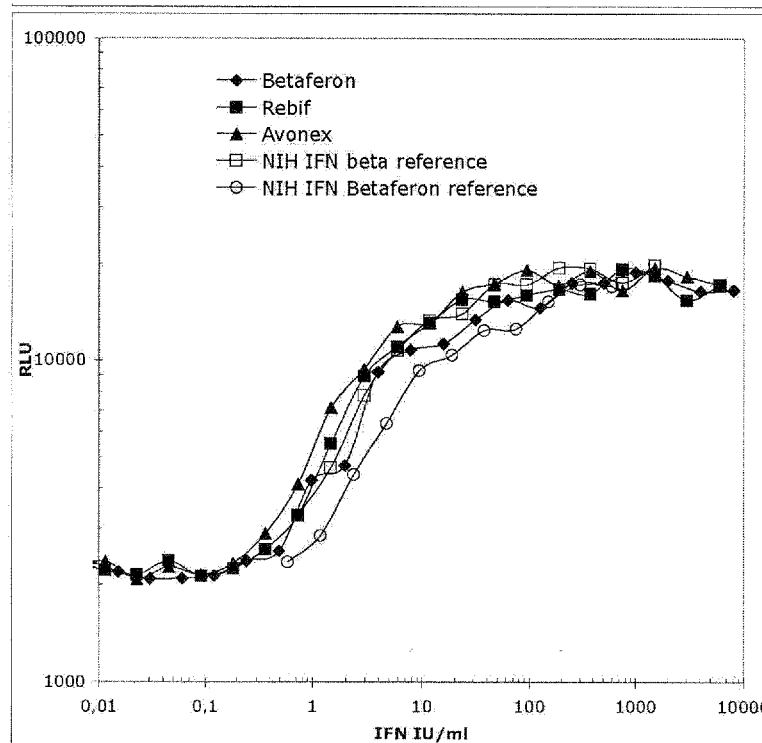
Figure 6A:
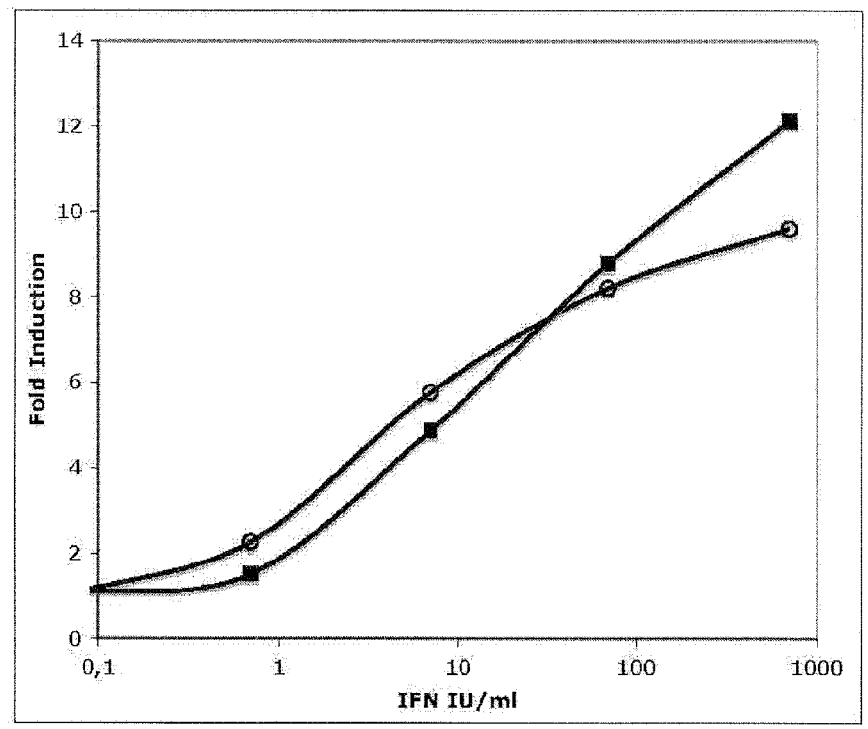
FIGS. 6A-6D are graphs comparing the dose-response curves for human type I interferons obtained using either chemically-treated or live cells. Assay-ready frozen PIL5 cells (open circle) or live PIL5 cells (solid square) were incubated overnight in duplicate with serial ten-fold dilutions of INTRONA™ (FIG. 6A), BETAFERON™ (FIG. 6B), REBIF™ (FIG. 6C), or AVONEX™ (FIG. 6D). Cells were then lysed with the luciferase substrate containing reagent and luciferase activity was determined using a luminometer as described in the Materials and Methods of Example 2. IFN activity was determined from the dose-response curve of relative luciferase units (RLU), expressed as fold induction, against IFN concentration expressed as IU/ml.
Figure 6B:
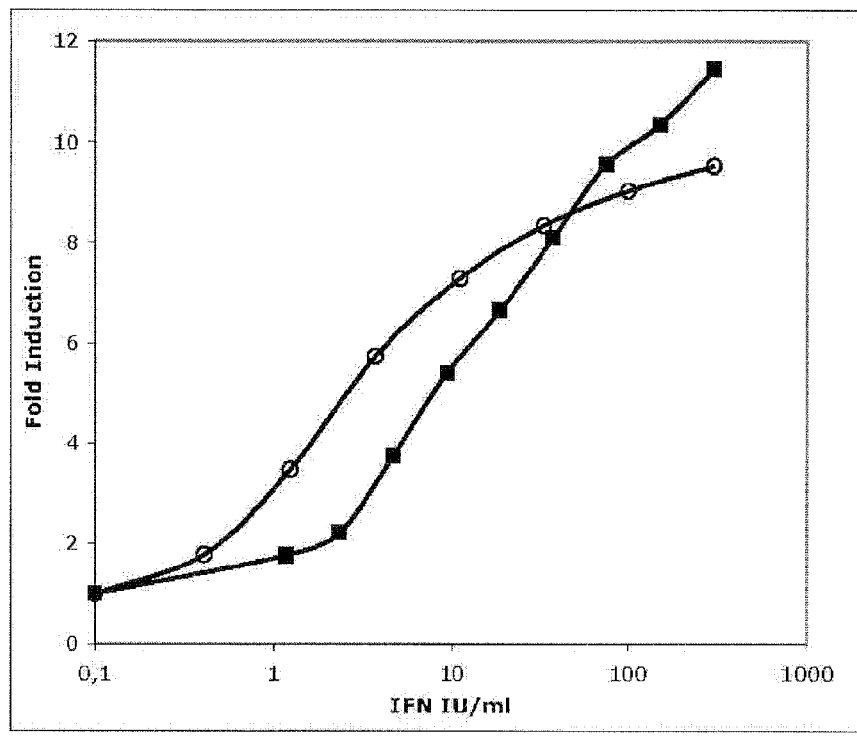
Figure 6C:
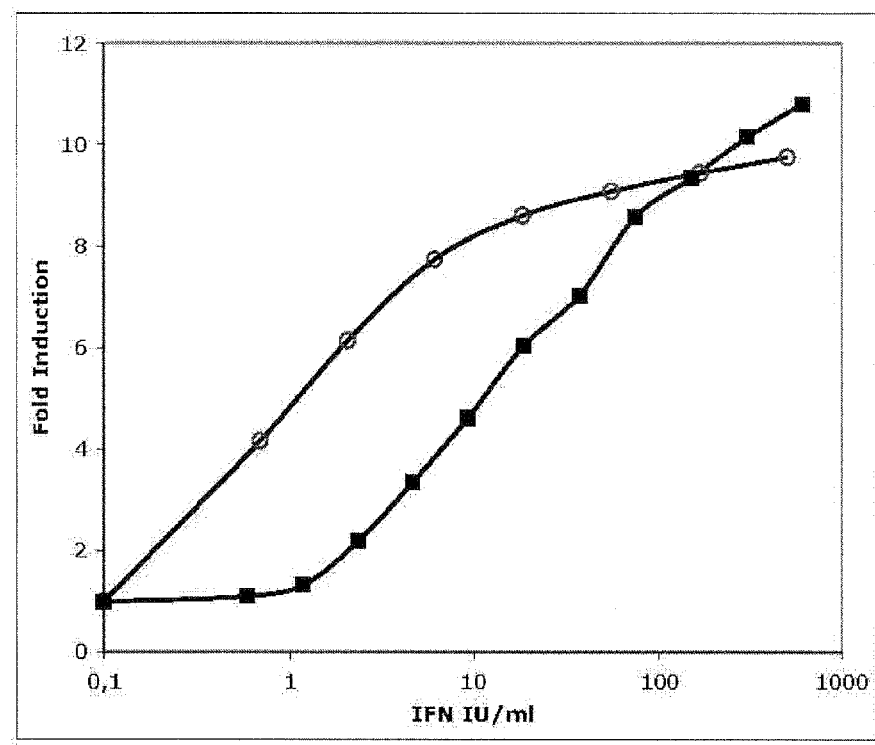
Figure 6D:
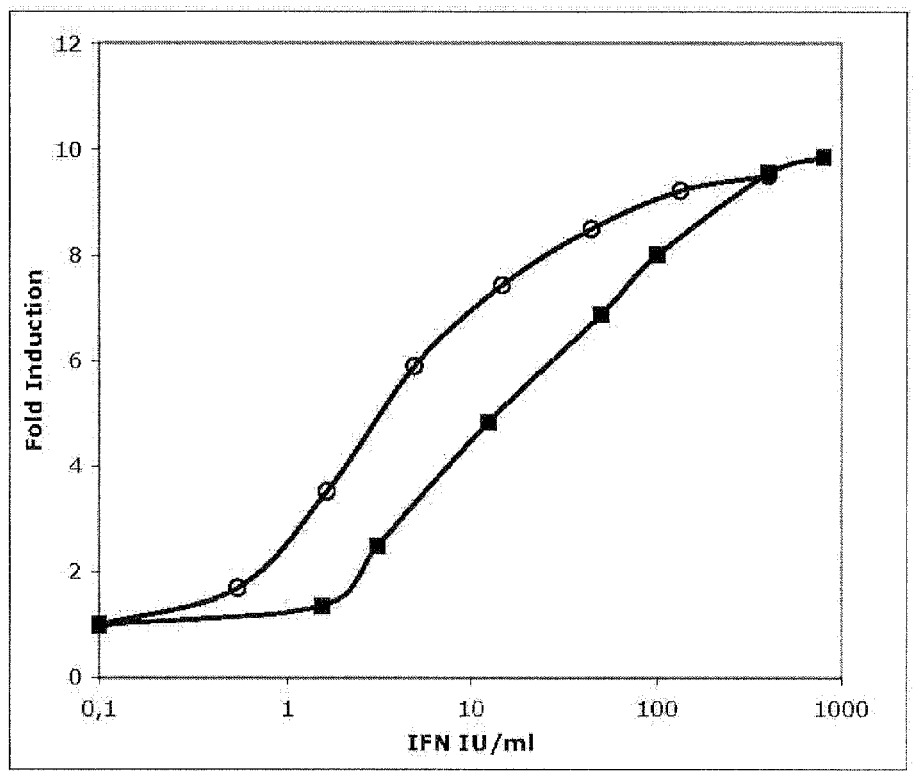
Figure 7A:
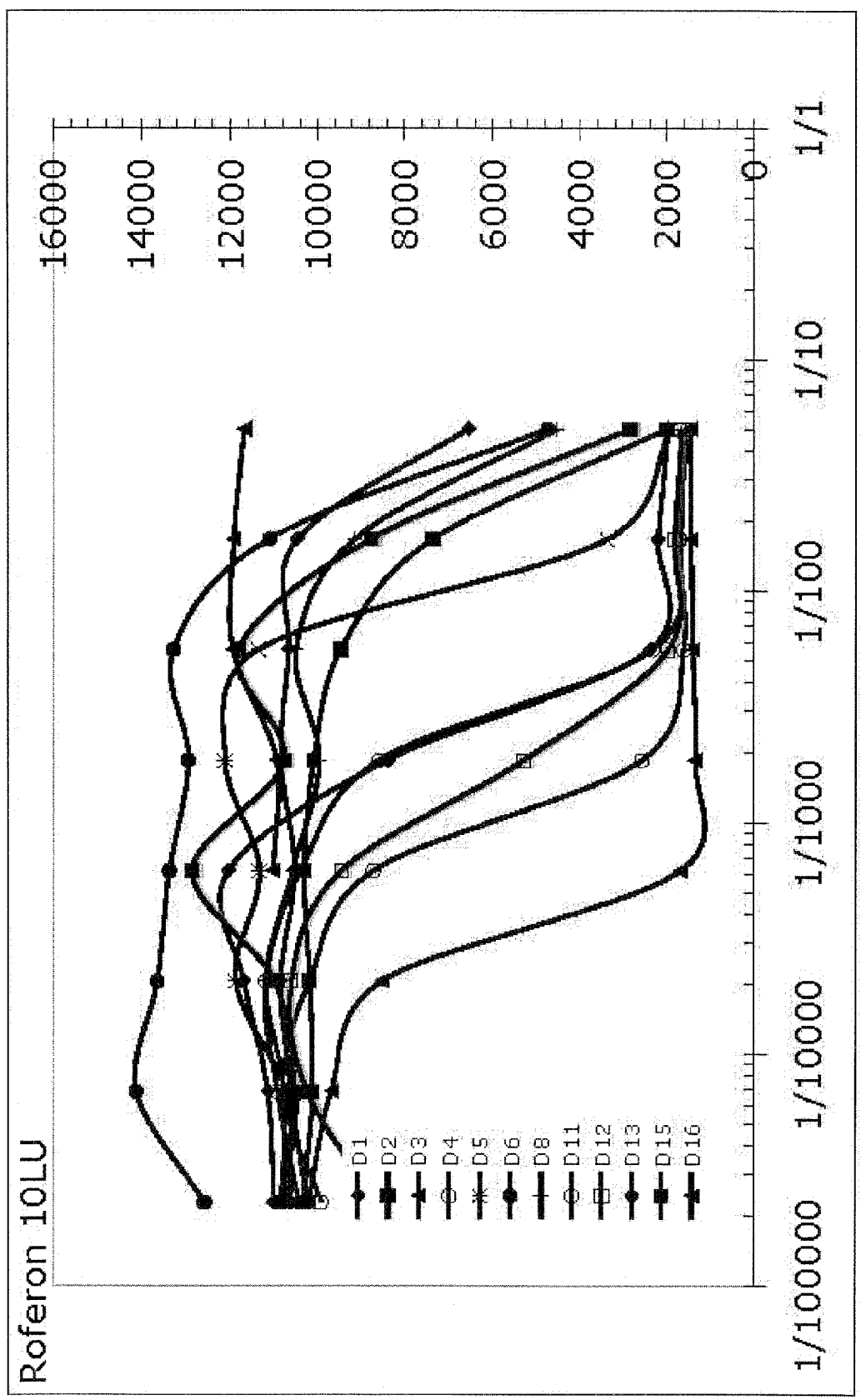
FIGS. 7A-7D are graphs of neutralization curves for anti-human IFN-α NABS using chemically treated PIL5 cells. Serial ten-fold dilutions of sera from patients with chronic hepatitis C treated with recombinant IFN-α2 were incubated in duplicate with 10 LU/ml of ROFERON™ (FIG. 7A), IFNα1 (FIG. 7B), PEGASYS™ (FIG. 7C), or PEG-INTRON™ (FIG. 7D) for 1 hour at 37° C. followed by 2 hours at 4° C. prior to incubation overnight with vinblastin-treated frozen PIL5 cells as described in the Materials and Methods of Example 2. Cells were then lysed with the luciferase substrate containing reagent and luciferase activity was determined using a luminometer as described in the Materials and Methods. The NAB titers of samples were determined as described in the Materials and Methods and expressed in TRU/ml.
Figure 7B:
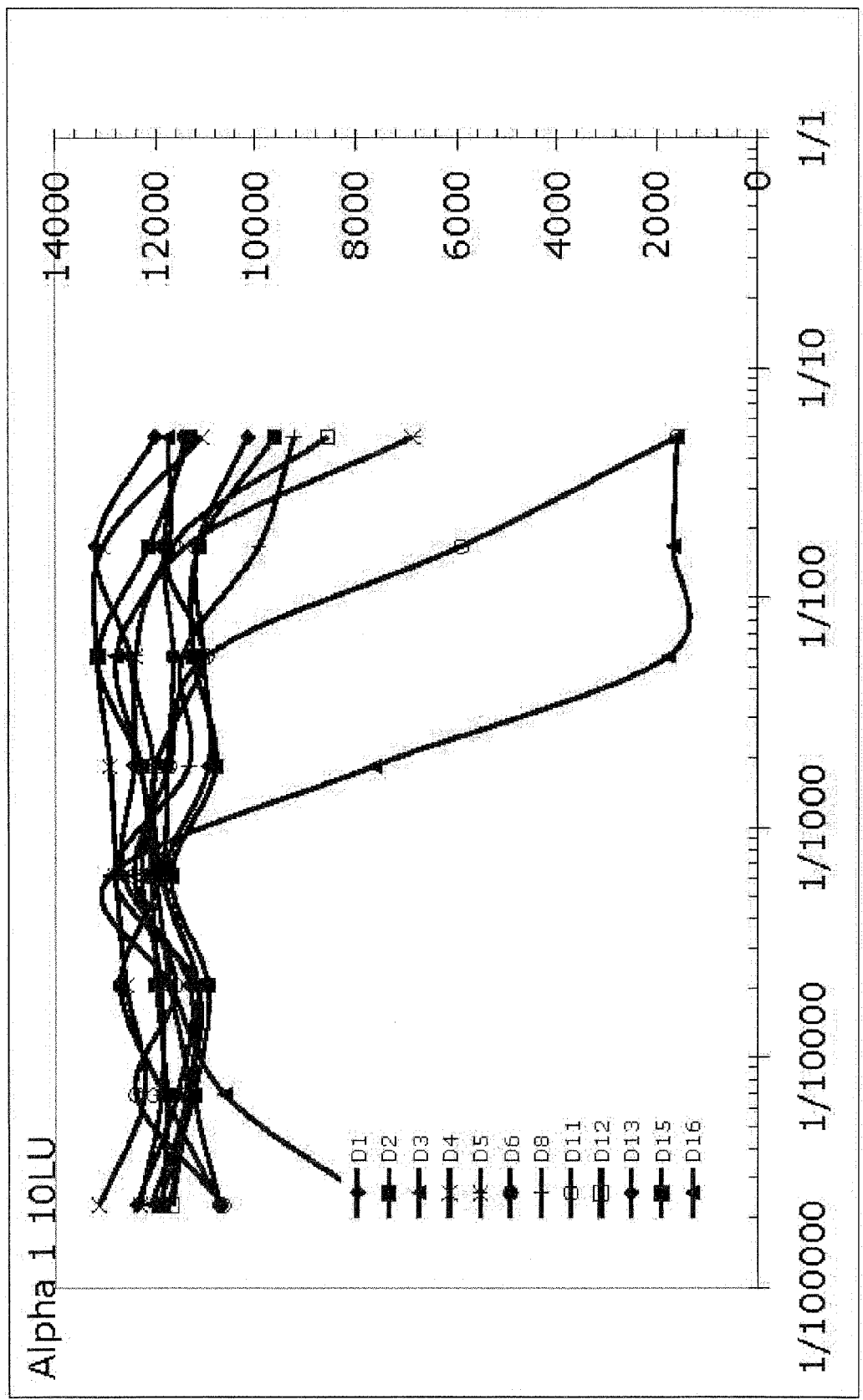
Figure 7C:
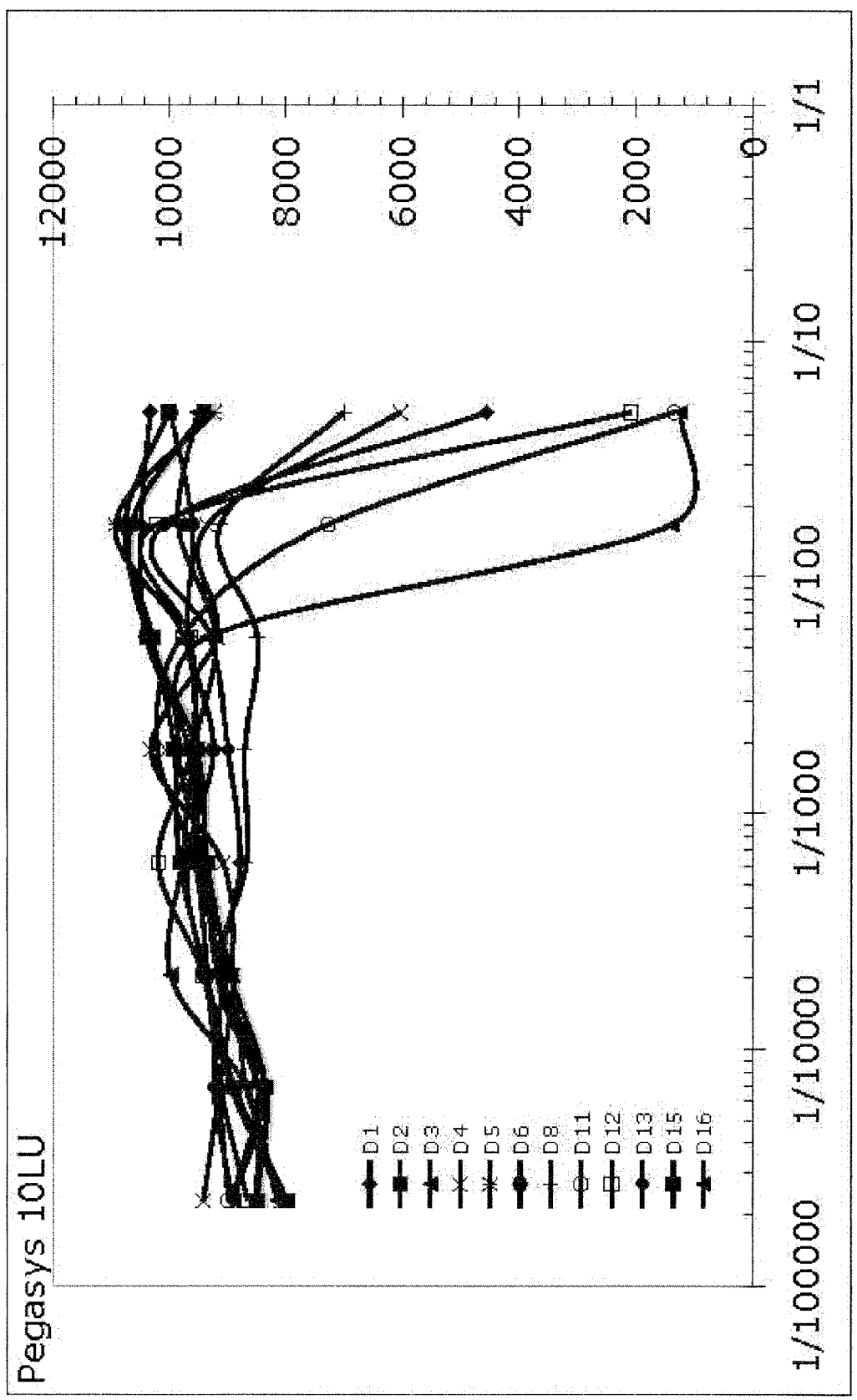
Figure 7D:
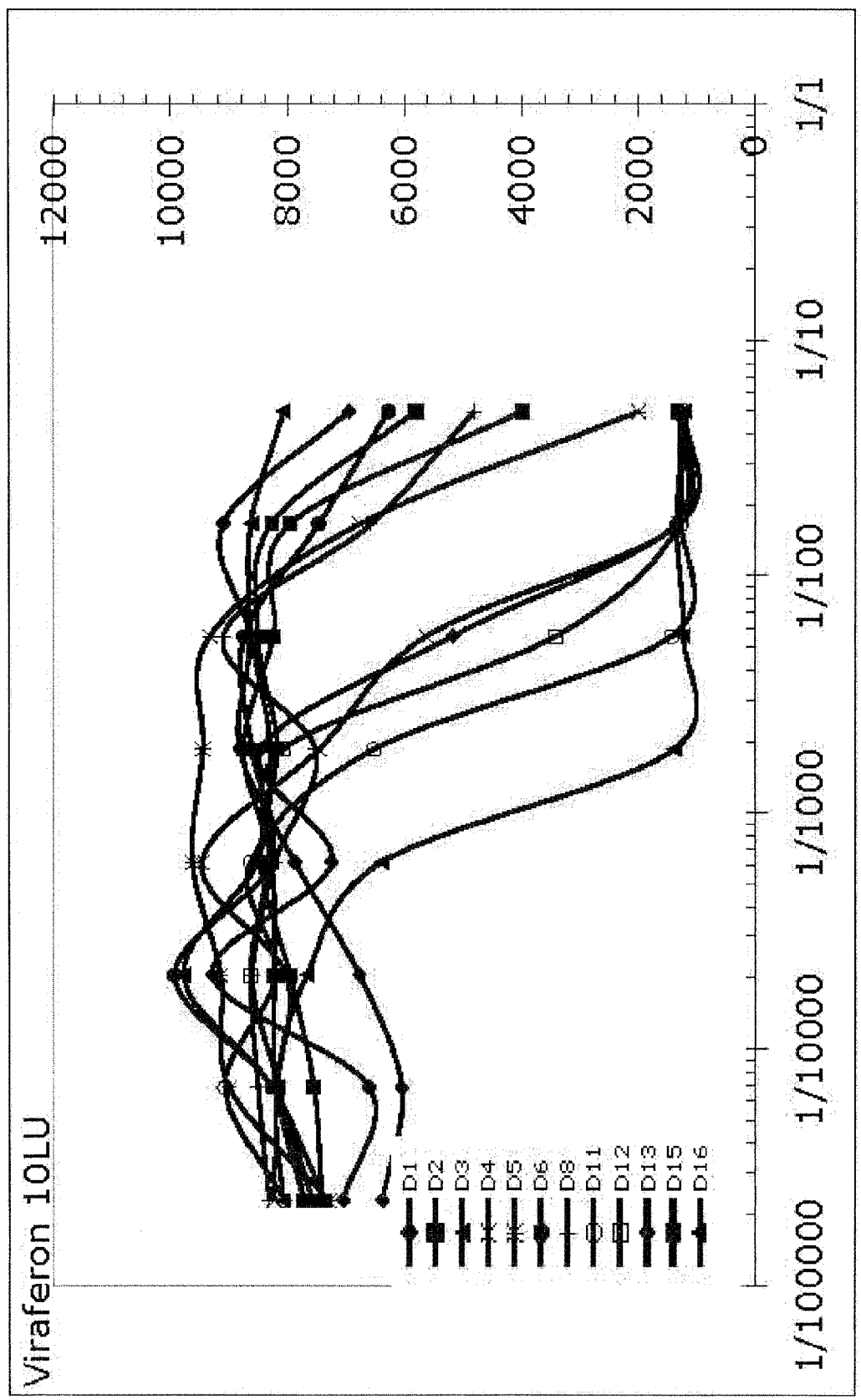

The IFN activity of clinically formulated preparations of IFNβ-1a (AVONEX), IFNβ1-a (REBIF), and IFNβ1-b (BETASERON) determined using the iLite gene-reporter assay (FIG. 5B) corresponded well with both the values obtained using an anti-viral bioassay (HuH7 cells/VSV) and those reported by the manufacturers (data not shown).

The PIL5 gene-reporter assay can detect human type I IFNs even in the presence of low concentrations of human IFNγ since human IFNγ exhibits 10% or less cross reactivity in this assay (data not shown).

Vinblastin treated division-arrested frozen PIL5 cells were found to exhibit a higher degree of sensitivity, defined as the mid-point of the IFN dose-response curve (1.0 LU/ml), a lower limit of IFN detection, and in some cases a slightly lower range of detection, than untreated PIL5 cells (FIGS. 6A-6D). Thus, for three different clinically formulated preparations of IFNβ (AVONEX, REBIF, and BETAFERON), 1.0 LU/ml was equivalent to 2.5, 1.0, and 3.0 IU/ml respectively for vinblastin treated cells compared with 10, 10, and 11 IU/ml for untreated cells (FIGS. 6A-6D). Similarly, the lower limit of detection for AVONEX, REBIF, and BETAFERON, was 0.2, 0.2, and 0.5 IU/ml, respectively, for vinblastin treated cells compared with 1.5, 1.5, and 2.0 IU/ml, respectively, for untreated PIL5 cells (FIGS. 6A-6D).

Determination of the Neutralizing Activity of a Polyclonal Anti-IFN α/β Antiserum Using the iLite Gene-Reporter Assay The iLite gene-reporter assay was used to determine the neutralizing titer of a sheep polyclonal anti-human IFNα/β antiserum. Briefly, serial-dilutions of a polyclonal anti-human IFNα/β antiserum, prepared by immunizing a sheep with purified human lymphoblastoid IFN, were incubated with 10 laboratory units (LU)/ml of IFNα (INTRON A) or IFN β1-a (AVONEX) in a micro-titer plate for 1 hour at 37° C., followed by 2 hours at 4° C. Vinblastin treated frozen PIL5 cells were then added to the antibody-IFN mixture and incubated overnight at 37° C. The neutralizing titer was then determined from the reciprocal of the antibody dilution that reduced IFN activity from 10 to 1.0 LUnits/ml (Kawade method). The anti-IFNα and anti-IFNβ neutralizing titers obtained for the sheep polyclonal anti-IFNα/β antiserum using the PIL5 gene-reporter assay were in good agreement with those obtained using the VSV/WISH antiviral bio-assay given that the antiviral bio-assay can only distinguish differences of two-fold or greater (Table 3).

TABLE 3

Comparison of the Neutralizing Titer of a Polyclonal Anti-human IFNα/β antibody obtained using the iLite assay with those obtained using a CPE assay

| | Polyclonal Anti-human IFN α/β Antiserum: Mean Neutralizing titer (TRU/ml) | |
|---|---|---|
| Interferon | VSV/WISH Bioassay | PIL5 Gene-Reporter Assay |
| IFN α-2b | 204,800 | 240,000 |
| IFN β-1a | 2,559 | 2,500 | the samples from untreated individuals, tested in the absence of added IFNα, were found to contain detectable levels of circulating IFNα (data not shown). In contrast, certain serum samples from patients with chronic hepatitis C treated with recombinant IFNα2, when tested in the absence of added IFNα, were found to contain detectable levels of circulating IFNα2 in the absence of anti-IFNα antibody (data not shown).

Serial dilutions of serum samples from patients with chronic hepatitis C treated with recombinant IFNα2 were incubated with 10 LU/ml of IFNα2a (ROFERON) or IFNα2-b (INTRON A) for 1 hour at 37° C. followed by 2 hours at 4° C. and then assayed for the presence of neutralizing antibodies against IFNα using vinblastin treated frozen PIL5 cells (FIGS. 7A-7D). Marked differences in neutralizing titers were observed between individual samples ranging from <20 to 3,500 TRU/ml determined using the Kawade methodology (Table 4). The NAB titers of samples of auto-antibodies to IFNα determined using the iLite assay were found to be in close agreement to the values obtained using an anti-viral bioassay (HuH7 cells/VSV) when assayed blinded (data not shown).

The neutralizing titers of sera from patients treated with IFNα2a (ROFERON) were found to be identical when assayed against either IFNα2a (ROFERON) or IFNα2b (INTRON A) using the iLite gene-reporter assay (data not shown). Similarly, the neutralizing titers of sera from patients treated with IFNα2b (INTRON A) were identical when assayed against either IFNα2a (ROFERON) or IFNα2b (INTRON A) using the iLite gene-reporter assay (data not shown). The neutralizing titers of sera from patients treated with either IFNα2a or IFNα2b were markedly different, however, when assayed against IFNα1 (Table 4).

TABLE 4

Comparison of Titers of Anti-IFNα NAbs Obtained with Doses of Antigen either as IFN Protein Mass or as 10 Functional Laboratory Units (LU)

| | | Interferon | | | | | | |
|---|---|---|---|---|---|---|---|---|
| | | 10 LU/ml | | | | 250 pg/ml | | |
| Therapy | Serum N° | Intron A | IFNα1 | PEG-Intron | Pegasys | Intron A | IFNα1 | PEG-Intron | Pegasys |
| Intron A | D1 | 400 | <20 | 150 | 20 | 500 | 8000 | 1000 | 1000 |
| Intron A | D2 | 40 | <20 | <20 | <20 | 50 | 60 | 100 | 200 |
| Intron A | D3 | <20 | <20 | <20 | <20 | <20 | <20 | <20 | <20 |
| Intron A | D4 | 400 | <20 | 150 | 10 | 650 | 700 | 1000 | 1000 |
| Intron A | D5 | 100 | 20 | 35 | <20 | 150 | 200 | 180 | ND |
| Intron A | D6 | 30 | <20 | <20 | <20 | 40 | 80 | 40 | 70 |
| Intron A | D8 | 30 | <20 | <20 | <20 | ND | ND | ND | ND |
| Intron A | D11 | 1,000 | 70 | 350 | 40 | 1500 | 4000 | 3000 | 3000 |
| Intron A | D12 | 700 | <20 | 250 | 30 | 1000 | 800 | 1500 | 1000 |
| Intron A | D13 | 20 | <20 | <20 | <20 | 35 | <20 | 20 | 40 |
| Intron A | D15 | 50 | <20 | 25 | <20 | 45 | <20 | 80 | 50 |
| Intron A | D16 | 3,500 | 450 | 1,000 | 100 | 8000 | 5000 | 10000 | 10000 |

ND: Not determined

Determination of Neutralizing Activity of Human Anti-IFN α Auto-Antibodies Using the iLite Gene-Reporter Assay.

The presence of human serum from normal volunteers at a concentration corresponding to a final dilution of 1:4 in the iLite gene-reporter assay gave RLU values identical to those obtained for untreated control samples (data not shown). Similarly, the presence of human serum from normal volunteers at a final dilution of 1:4 had no effect on the IFN titer of IFNα2-b (INTRON A) or IFN β1-a (data not shown). None of In contrast, when the neutralizing assay was carried out using a constant quantity (250 pg/ml) of IFNα1 or IFNα2 (ROFERON or INTRON A) protein, comparable neutralizing titers were obtained for a given serum (Table 4). Similarly, the neutralizing titers of sera from patients treated with either IFNα2a or IFNα2b were markedly different when assayed against 10 LU/ml of pegylated IFNα2a (PEGASYS™) and to a lesser extent against IFNα2b (PEG-INTRON™) which exhibit lower specific activities than their respective native molecules (Deisenhammer et al., 2004).

Thus, the neutralizing titers of sera from patients treated with either IFNα2a or IFNα2b were consistently lower when assayed against PEG-INTRON™ and markedly lower when assayed against PEGASYS™ (Table 4). In contrast, similar neutralizing titers were obtained when the same sera were assayed against 250 pg of IFNα2a (ROFERON™), PEG-INTRON™ or pEGASYS™ (Table 4). None of the sera from patients treated with either IFNα2a (ROFERON) or IFNα2b (INTRON A) neutralized IFN β1-a (data not shown), or IFNβ1-b (Table 4).

Determination of Neutralizing Activity of Human Anti-IFN β Auto-Antibodies Using the iLite Gene-Reporter Assay.

The presence of human serum from normal volunteers at a final dilution of 1:4 had no effect on the IFN titer of two different preparations of IFNβ1-a, AVONEX and REBIF, determined using the iLite assay (data not shown). Certain serum samples from patients treated with IFNβ, when tested in the absence of added IFN, were found to contain detectable levels of circulating IFN in the absence of anti-IFNβ antibody (data not shown).

Figure 8A:
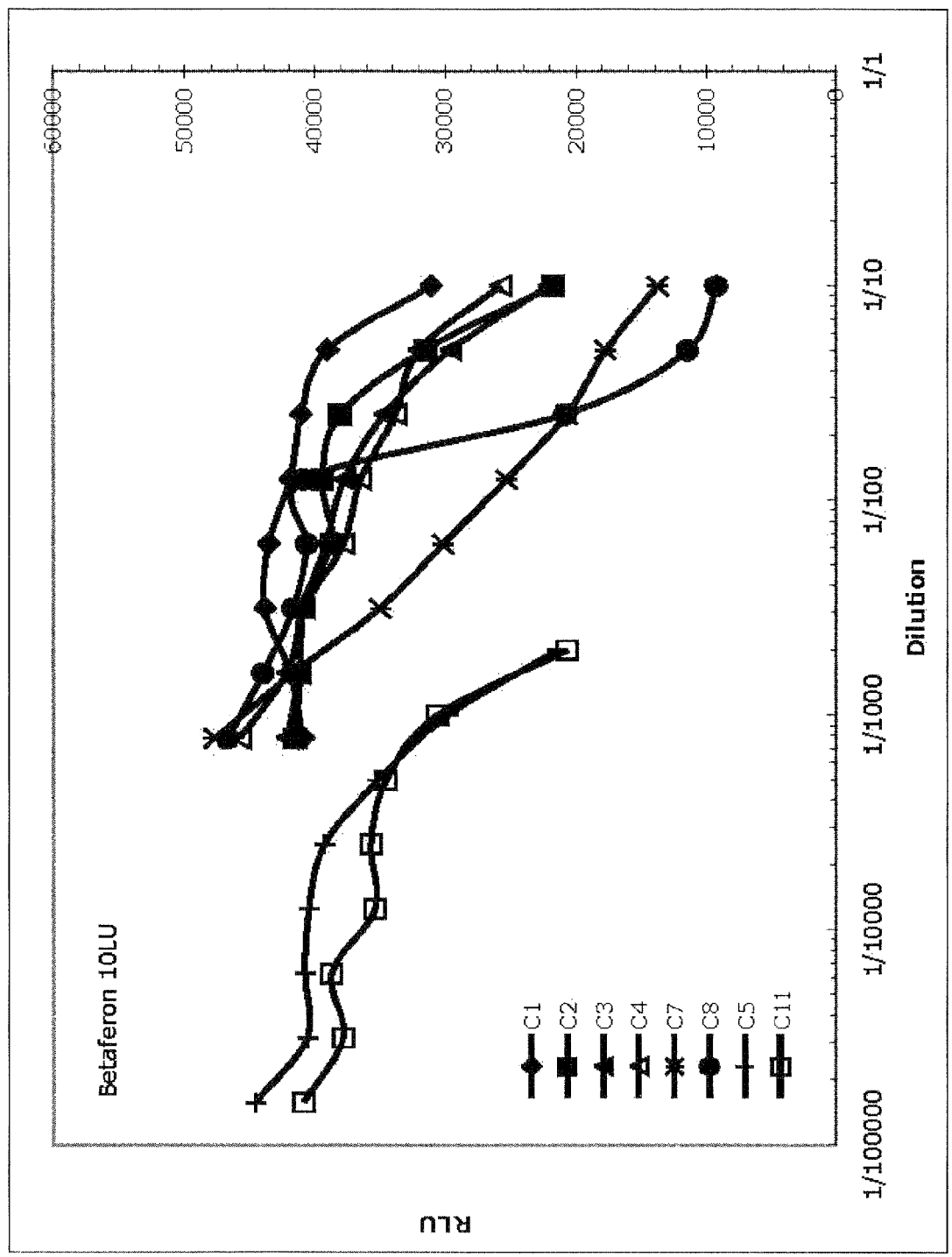
FIGS. 8A-8C are graphs of neutralization curves for anti-human IFN-β NABS using chemically treated PIL5 cells. Serial ten-fold dilutions of sera from patients with RRMS treated with recombinant IFNβ were incubated in duplicate with 10 LU/ml of BETAFERON™ (FIG. 8A), REBIF™ (FIG. 8B), or AVONEX™ (FIG. 8C), for 1 hour at 37° C. followed by 2 hours at 4° C. prior to incubation overnight with vinblastin-treated frozen PIL5 cells as described in the Materials and Methods of Example 2. Cells were then lysed with the luciferase substrate containing reagent and luciferase activity was determined using a luminometer as described in the Materials and Methods of Example 2. The NAB titers of samples were determined as described in the Materials and Methods and expressed in TRU/ml.
Figure 8B:
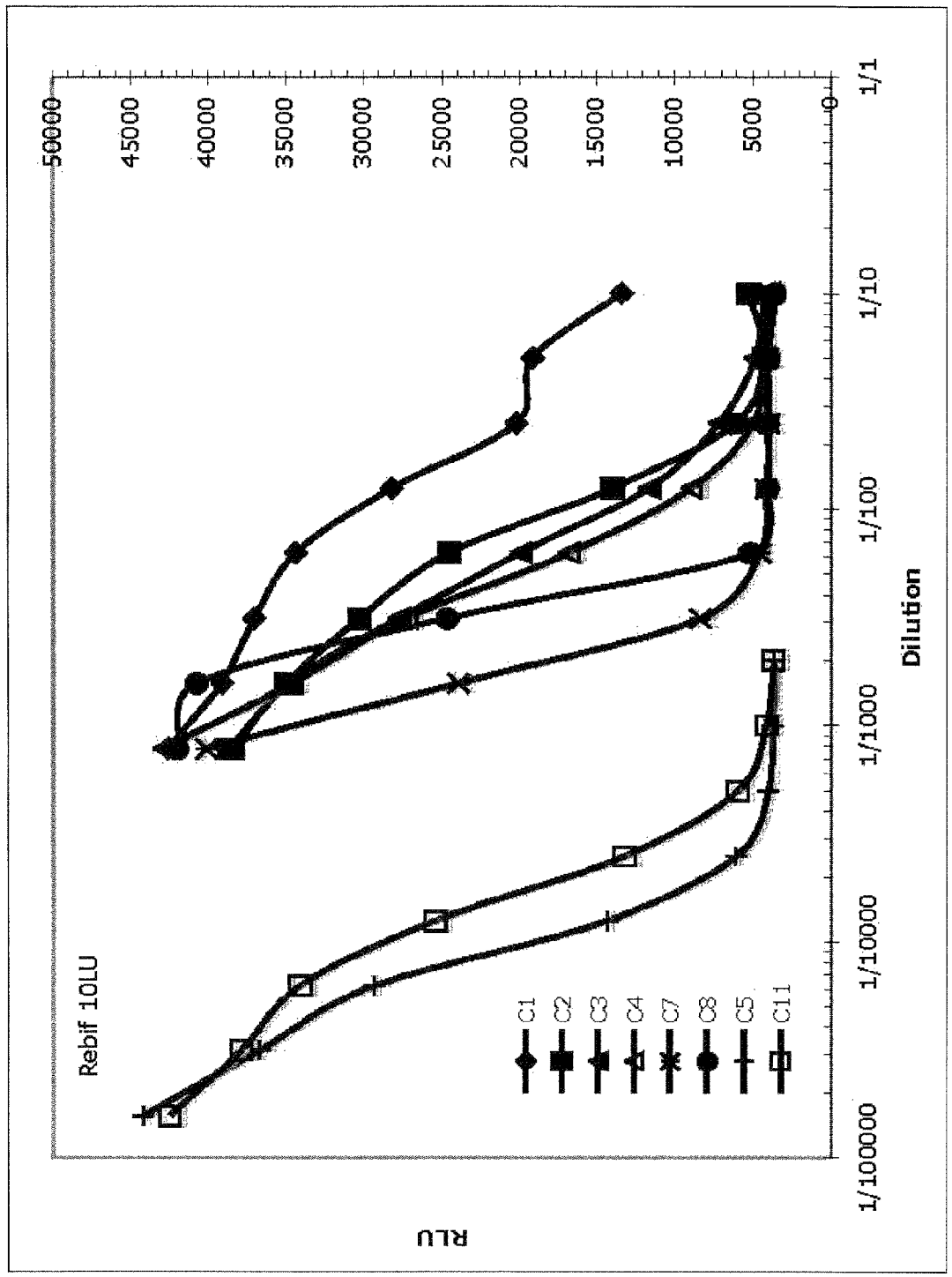
Figure 8C:
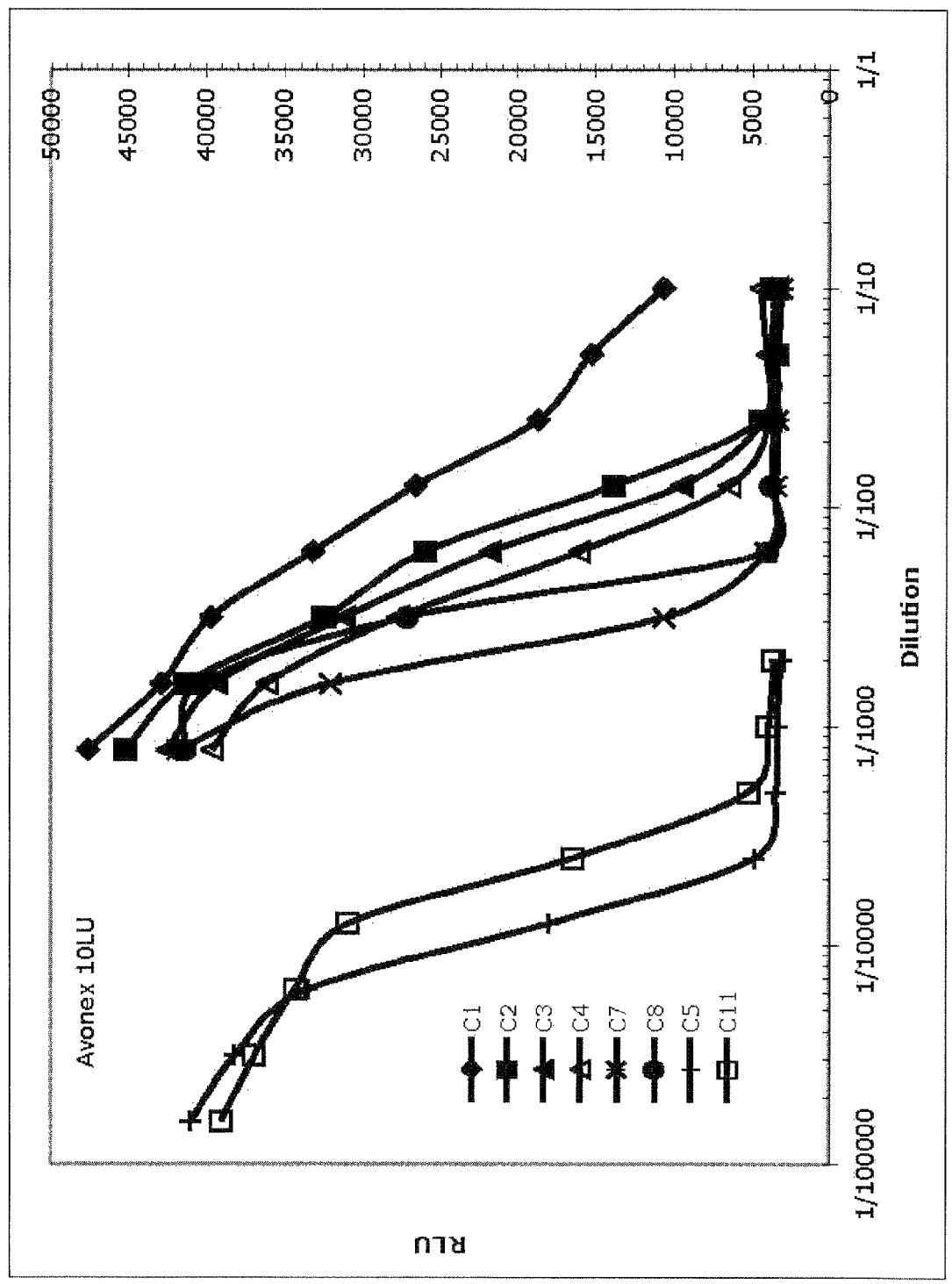

Serial dilutions of serum samples from patients treated with recombinant IFNβ were incubated with 10 LU/ml of IFNβ1-a (AVONEX or REBIF) or 10 LU/ml of IFNβ1-b (BETAFERON) and then assayed for the presence of neutralizing antibodies against IFNβ using the iLite test as described in the Materials and Methods (FIG. 8A-8C). The NAB titers of samples determined using the iLite assay and the same IFN preparation used to treat the patient were found to be in close agreement to the values obtained using an anti-viral bioassay when assayed blinded (Data not shown). NAB titers ranged from <10 to 150,000 TRU/ml. The neutralizing titers of sera from patients treated with IFNβ1-a (AVONEX or REBIF) were identical or closely similar when assayed against 10 LU/ml of either AVONEX or REBIF but were markedly different when assayed against 10 LU/ml of IFNβ1-b (BETAFERON) as shown in Table 5. In contrast, when the neutralizing assay, was carried out using a constant quantity (50 pg/ml) of IFNβ1-a (AVONEX or REBIF) or IFNβ1-b (BETAFERON) protein, identical or similar neutralizing titers were obtained for a given serum when assayed using any one of the three IFNβ subtypes (Table 5). Furthermore, when a constant quantity (50 pg/ml) of IFNβ protein was used in the neutralization assay, the titers obtained for a given serum sample from a patient treated with either IFNβ1-a (AVONEX or REBIF) or IFNβ1-b (BETAFERON) were similar when the assay was performed using either the same IFN used to treat the patient or a different IFNβ sub-species (Table 5).

None of the serum samples from patients treated with recombinant IFNβ, whether IFNβ1-a (AVONEX or REBIF) or IFNβ1-b (BETAFERON), neutralized IFNα2a (ROFERON) or IFNα2b (INTRON A) (Data not shown).

TABLE 5

Comparison of Titers of Anti-IFNβ NAbs Obtained with Doses of Antigen either as IFN Protein Mass or as 10 Functional Laboratory Units (LU)

| Therapy | Serum N° | Interferon | | | | | |
| --- | --- | --- | --- | --- | --- | --- | --- |
| | | 10 LU/ml | | | 50 pg/ml | | |
| | | Betaferon | Rebif | Avonex | Betaferon | Rebif | Avonex |
| Betaferon | C1 | 25 | 100 | 100 | 25 | 40 | 25 |
| Betaferon | C2 | 100 | 350 | 400 | 100 | 150 | 150 |
| Betaferon | C3 | 150 | 700 | 900 | 150 | 200 | 250 |
| ND | C4 | 200 | 900 | 1,000 | 200 | 300 | 200 |
| Betaferon | C5 | 15,000 | 50,000 | 50,000 | 15,000 | 15,000 | 10,000 |
| Rebif | C6 | <20 | <20 | <20 | <20 | <20 | <20 |
| Betaferon | C7 | 600 | 3,500 | 4,000 | 600 | 700 | 500 |
| Betaferon | C8 | 300 | 7,000 | 2500 | 300 | 400 | 350 |
| Rebif | C9 | <20 | <20 | <20 | <20 | <20 | <20 |
| Betaferon | C10 | <20 | <20 | <20 | <20 | <20 | <20 |
| Avonex | C11 | 7,000 | 35,000 | 25,000 | 7,000 | 8,000 | 10,000 |
| Betaferon | C12 | 150 | 2,000 | 1,200 | 150 | 150 | 150 |
| ND | C13 | 4,000 | 40,000 | 24,000 | 4,000 | 6,000 | 6,000 |
| Betaferon | C14 | 200 | 2,500 | 2,500 | 200 | 200 | 300 |
| Avonex | B1 | <20 | <20 | <20 | <20 | <20 | <20 |
| Betaferon | B2 | <20 | <20 | <20 | <20 | <20 | <20 |
| Avonex | B3 | <20 | <20 | <20 | <20 | <20 | <20 |
| Avonex | B4 | <20 | <20 | <20 | <20 | <20 | <20 |
| Rebif | B5 | <20 | <20 | <20 | <20 | <20 | <20 |
| ND | B6 | 150 | 700 | 700 | 150 | 150 | 150 |
| Rebif | B7 | 100 | 700 | 450 | 100 | 200 | 200 |
| Rebif | B8 | 400 | 4,000 | 4,000 | 400 | 1,000 | 900 |
| Betaferon | B9 | <20 | 80 | 30 | <20 | <20 | <20 |
| ND | B10 | <20 | 25 | 20 | <20 | <20 | <20 |
| ND | B11 | 30 | 300 | 400 | 30 | 35 | 35 |

ND: Not determined

Discussion

Repeated administration of recombinant homologues of human proteins can result in a break in immune tolerance to self-antigens resulting in the production of auto-antibodies as in the case of the interferons, IL-2, GM-CSF, and EPO (Schellekens, 2003). Auto-antibodies to IFNα that occur in patients with chronic hepatitis C treated with recombinant IFNα are for the most part binding antibodies without any apparent untoward consequences for the patient. In patients with RRMS treated with IFNβ neutralizing antibodies occur in a significant proportion of patients, however, and are associated with a reduced therapeutic effect and disease progression (Hartung et al., 2007; Noronha, 2007; and Namaka et al., 2006). Detection of neutralizing antibodies requires the use of cell-based assays that are often based on imprecise end-points such as inhibition of cell proliferation or inhibition of viral cytopathic effect (Meager, 2006). In an attempt to obtain a more precise bioassay for human type I IFNs, a stable transfectant carrying the luciferase reporter-gene controlled by an IFN responsive chimeric promoter was isolated which allows IFN activity to be determined selectively, and with a high degree of precision within a few hours. Bioassays based on the use of continuously cultivated cell-lines are subject to considerable variation, however, due both to genetic instability with increasing passage number and variation in culture conditions (Meager, 2006), irrespective of whether the end-point measured is CPE, MxA or a reporter gene activity. Thus, in order to obviate assay variation associated with the use of continuously cultivated cell-lines, master and working cell-banks were established and conserved in liquid nitrogen. Cells were then thawed, amplified for a constant number of passages under standardized conditions and then treated with the anti-mitotic drug vinblastin. This allows assay-ready cells to be stored frozen at −80° C. for extended periods (>3 years) without loss of IFN sensitivity or the need for cell culture. The production of cells under rigorously controlled conditions and at a constant passage number, by the manufacturer rather than the end user, eliminates assay variation associated with epigenetic and genetic changes and changes in cell culture conditions that occur when cells are cultivated continuously in different laboratories. Division-arrested frozen PIL5 cells were found to perform as well as, and in some aspects better, than untreated PIL5. For example vinblastin-treated cells exhibited a higher degree of IFN sensitivity and a lower limit of detection of IFN activity than untreated cells. The PILS assay can be readily automated and is ideally suited for high throughput screening for IFN activity or the presence of neutralizing anti-IFN antibodies.

The IFN activity of a number of well characterized preparations of human IFNα and IFNβ, determined using the PIL5 gene-reporter assay, were in close agreement with the values obtained using an anti-viral bioassay. This was equally true for native IFNs or their pegylated variants. It is of interest that closely similar results were obtained using a gene-reporter assay based on the use of the IFN specific recognition sequence from the ISG15 gene, an IFN regulated gene that encodes a 17 Da ubiquitin-like modifier protein involved in innate immunity (Ritchie et al., 2004; and Dao et al., 2005), to those obtained using an assay based on inhibition of virus cytopathic effect which most probably reflects the effect of IFN on numerous individual genes.

The use of the PIL5 gene-reporter assay to detect and quantify neutralizing antibodies to human IFNα or IFNβ again yielded results closely similar to those obtained using an anti-viral bioassay. The use of the PIL5 gene-reporter assay revealed marked differences in neutralizing titer, however, when IFNs other than those used to treat the patient were used to assay neutralizing titer in vitro. This was observed both when IFNα1 or pegylated IFNα2a (PEGASYS™), were used to assay NABs from patients treated with IFNα2a (ROFERON™) or IFNα2b (INTRON A™) and when IFNβ1-b (BETAFERON™) was used to assay NABs from patients treated with IFNβ1-a (AVONEX™ or REBIF™). The specific activity of IFNα2a (ROFERON) and IFNα2b (INTRONA) are both approximately $2.0 \times 10^8$ IU/mg, that is ten fold or greater than that of either IFNα1 ($1.0 \times 10^7$ IU/mg) or pegylated IFN-α2a.

According to the manufacturer's specifications, the specific activity of the two clinically formulated preparations of IFNβ1-a, AVONEX or REBIF, are 2.0 and $2.7 \times 10^8$ IU/mg respectively, while that of IFNβ1-b (BETASERON) is approximately $3.2 \times 10^7$ IU/mg. Thus, given the differences in specific activity of IFNα1 or pegylated IFNα2a compared with IFNα2, and the differences in specific activity between IFNα1-a, and IFNα1-b, the use of a constant number of activity units of either the different IFNα or different IFNβ preparations will result in markedly different quantities of IFN protein in the antibody-antigen neutralization reaction. It is of interest that closely similar neutralization titers were obtained, however, when the same concentration of IFNα protein (IFNα1 or IFNα2), or IFNβ protein (IFNα1-a or IFNβ1-b), was used in the neutralization assay rather than a constant number of activity units per ml. These results suggest that neutralization titer is dependent upon the relative concentration of antigen to antibody in the neutralization assay rather than IFN activity, or differences in the specificities of the auto-antibodies assayed.

Auto-antibodies to IFNα, detected in the sera of patients treated with IFNα2, cross-neutralized all the IFNα preparations tested (IFNα1, IFNα2a, IFNα2b, PEGASYS™, PEG-INTRON™) but did not neutralize any of the clinically formulated IFNβ preparations (AVONEX™, REBIF™, or BETAFERON™) tested. Similarly, auto-antibodies to IFNβ, detected in the sera of patients treated with IFNα1-a or IFNβ1-b did not cross neutralize any of the IFNα preparations tested. This lack of cross-neutralization may explain the absence of apparent untoward effects of IFN auto-antibodies in patients treated with recombinant IFNs in marked contrast to the life-threatening complications associated with the presence of auto-antibodies to erythropoietin or thrombopoietin which can result in pure red cell aplasia and thrombocytopenia respectively (Schellekens, 2003). The development of NABs to IFNβ is associated, however, with a reduced clinical response and disease progression in patients with multiple sclerosis (Hartung et al., 2007; Noronha, 2007; and Namaka et al., 2006). A number of reports have suggested that patients with RRMS should be monitored every 6 to 12 months for NABs to IFNβ (Hartung et al., 2007; and Sorensen et al., 2005). Alternative therapies such as glatiramer acetate and natalizumab, a monoclonal antibody that binds to the alpha4 subunit of the alpha4B1 integrin (Rudick et al., 2006), are available for patients no longer able to respond to IFNβ therapy following the development of anti-IFNβ NABs. The use of vinblastin-treated frozen PIL5 cells offers distinct advantages over existing IFN assays for the characterization of anti-IFN NABs, and provides the basis for an assay that can be readily automated, and is ideally suited for screening for anti-IFN NABs.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abramovich et al. (1994) Differential tyrosine phosphorylation of the IFNAR chain of the type I interferon receptor and of an associated surface protein in response to IFN-alpha and IFN-beta. *Embo J.* 13:5871.

Alton et al. (1979) Nucleotide sequence analysis of the chloramphenicol resistance transposon Tn9. *Nature* 282: 864-869

Ank et al JICR 2006, 26:373-379

Antonetti F, Finocchiaro O, Mascia M, Terlizzese M G, Jaber A. J. *Interferon & Cytokine Res.* (2002) 22:1181-1184.

Baldwin et al. (1984) Cloning of the luciferase structural genes from *Vibrio harveyi* and expression of bioluminescence in *Escherichia coli. Biochemistry* 23:3663-3667

Barbieri et al. (1994) Activation of the protein tyrosine kinase tyk2 by interferon alpha/beta. *Eur J. Biochem.* 223:427.

Basu et al. (1998) The antiviral action of interferon is potentiated by removal of the conserved IRTAM domain of the IFNAR1 chain of the interferon alpha/beta receptor: effects on JAK-STAT activation and receptor down-regulation. *Virology.* 242:14.

Bazan, (1990). Structural design and molecular evolution of a cytokine receptor superfamily. *Proc Natl Acad Sci USA.* 87:6934.

Bertolotto A, Malucchi S, Sala A, Orefice G. Carrieri P B, Capobianco M, Milano E, Melis F, Giordana M T. *J. Neuro Neurosurg. Psychiatry,* (2002) 73:148-153.

Bouche et al. (1987) Basic fibroblast growth factor enters the nucleolus and stimulates the transcription of ribosomal genes in ABAE cells undergoing G0 - - - G1 transition. *Proc. Natl Acad. Sci. U.S.A.* 84:6770-6774

Boulter et al. (1986) Isolation of a cDNA clone coding for a possible neural nicotinic acetylcholine receptor alpha-subunit. *Nature* 319:368-374

Boulter et al. (1990) Alpha 3, alpha 5, and beta 4: three members of the rat neuronal nicotinic acetylcholine receptor-related gene family form a gene cluster. *J. Biol. Chem.* 265:4472-4482

Branca et al. (1981) Evidence that types I and II interferons have different receptors. *Nature.* 294:768.

Bunzow et al. (1988) Cloning and expression of a rat D2 dopamine receptor cDNA. *Nature* 336:783-787

Canosi et al. (1996) A highly precise reporter gene bioassay for type I interferon. *Journal of Immunological Methods* 199:69-76

Changelian et al. (1989) Structure of the NGFI-A gene and detection of upstream sequences responsible for its transcriptional induction by nerve growth factor. *Proc. Natl. Acad. Sci. USA* 86:377-381

Changelian et al. (1989) Structure of the NGFI-A gene and detection of upstream sequences responsible for its transcriptional induction by nerve growth factor. *Proc. Natl. Acad. Sci.* 86:377-381

Cleary et al. (1994) Knockout and reconstitution of a functional human type I interferon receptor complex. *Journal of Biological Chemistry.* 269:18747.

Clerico M, Contessa G. Durelli L. Interferon-beta 1a for the treatment of multiple sclerosis. *Expert Opin. Biol. Ther.* (2007) 7:535-542.

Cohen et al. (1995) Ligand-induced association of the type I interferon receptor components. *Mol Cell Biol.* 15:4208.

Colamonici et al. (1994) Direct binding to and tyrosine phosphorylation of the alpha subunit of the type I interferon receptor by p135tyk2 tyrosine kinase. *Mol. Cell. Biol.* 14:8133.

Comb et al. (1986) *Nature* 323:353-356

Constantinescu et al. (1994) Role of interferon alpha/beta receptor chain 1 in the structure and transmembrane signaling of the interferon alpha/beta receptor complex. *Proc Natl Acad Sci USA.* 91:9602.

Constantinescu et al. (1995) Expression and signaling specificity of the IFNAR chain of the type I interferon receptor complex. *Proc Natl Acad Sci USA.* 92:10487.

Cook et al. (1996) Differential responsiveness of a splice variant of the human type I interferon receptor to interferons. *J Biol. Chem.* 271:13448.

Cutrone et al. (1997) Contributions of cloned type I interferon receptor subunits to differential ligand binding. *FEBS Lett.* 404:197.

Dao C T, Zhang D E. ISG15/A ubiquitin-like enigma. *Front. Biosci.* (2005) 10:2701-2722.

Darnell et al. (1994) Jak-STAT pathways and transcriptional activation in response to IFNs and other extracellular signaling proteins. *Science.* 264:1415.

De Maeyer et al. (1988) Interferons and other regulatory cytokines. *John Wiley,* New york:69.

Deisenhammer F, Schellekens H, Bertolotto A. *J. Neurol.* (2004) 251(Suppl. 2):11:31-11:39.

Deneris et al. (1988) Primary structure and expression of beta 2: a novel subunit of neuronal nicotinic acetylcholine receptors. *Neuron* 1:45-54

Deneris et al. (1989) Beta 3: a new member of nicotinic acetylcholine receptor gene family is expressed in brain. *J. Biol. Chem.* 264: 6268-6272 deWet et al. (1987) Firefly luciferase gene: structure and expression in mammalian cells. *Mol. Cell. Biol.* 7:725-737

Diaz et al. (1993) Nomenclature of the human interferon genes. *J Interferon Res.* 13:443

Diebold S S, Kaisho T, Hemmi H, Akira S, Reis, E., and Sousa C. (2003). Innate antiviral responses by means of TLR7-mediated recognition of single-stranded RNA. *Science.* 303, 1529-1531.

Dixon et al. (1986) Cloning of the gene and cDNA for mammalian beta-adrenergic receptor and homology with rhodopsin. *Nature* 321:75-79

Domanski et al. (1995) Cloning and expression of a long form of the beta subunit of the interferon alpha beta receptor that is required for signaling. *J Biol. Chem.* 270:21606.

Domanski et al. (1996) The type-I interferon receptor. The long and short of it. *Cytokine Growth Factor Rev.* 7:143.

Duvoisin et al. (1989) The functional diversity of the neuronal nicotinic acetylcholine receptors is increased by a novel subunit: beta 4. *Neuron* 3:487-496

Ellis et al. (1988) Sequence and expression of mRNAs encoding the alpha 1 and alpha 2 subunits of a DHP-sensitive calcium channel. *Science* 241:1661-1664

Engebrecht et al. (1984) Identification of genes and gene products necessary for bacterial bioluminescence. *PNAS* 1:4154-4158

Fiette et al. (1995) Theiler's virus infection of 129Sv mice that lack the interferon alpha/beta or interferon gamma receptors. *Journal of Experimental Medicine.* 181:2069.

Fink et al. (1988), The CGTCA sequence motif is essential for biological activity of the vasoactive intestinal peptide gene cAMP-regulated enhancer. *Proc. Natl. Acad. Sci.* 85:6662-6666

Frielle et al. (1987) Cloning of the cDNA for the human beta 1-adrenergic receptor. *Proc. Natl. Acad. Sci.* 84:7920-7924

Fu, (1992) A transcription factor with SH2 and SH3 domains is directly activated by an interferon alpha-induced cytoplasmic protein tyrosine kinase(s). *Cell.* 70:323.

Giovannoni G. Optimizing MS disease-modifying therapies: antibodies in perspective. *J. Neurol.* (2004) 251(Supl. 5) v30-v35.

Goldman et al. (1987) Members of a nicotinic acetylcholine receptor gene family are expressed in different regions of the mammalian central nervous system. *Cell* 48:965-973

Grossberg S E, Kawade Y, Kohase M, Klein P. The neutralization of interferons by antibody. II; Neutralizing antibody unitage and its relationship to bioassay sensitivity: The tenfold reduction unit. *J. Interferon & Cytokine Res.* (2001a) 21:729-742.

Grossberg S E, Kawade Y, Kohase M, Yokoyama H, Finter N. The neutralization of interferons by antibody. I; Quantitative and theoretical analysis of the neutralization reaction in different systems. *J. Interferon & Cytokine Res.* (2001b) 21:729-742.

Hall et al. (1983) *J. Mol. Appl. Gen.* 2:101

Hammerling et al. (1998) The β-gal interferon assay: a new, precise, and sensitive method. *Journal of Interferon and Cytokine Research* 18:451-460

Hartung H P, Polman C, Bertolotto A, Deisenhammer F, Giovannoni G, Havrdova E, Hemmer B, Hillert J, Kappos L, Kieseier B, Killestein J, Malcus C, Comabella M, Pachner A, Schellekens H, Sellebjerg F, Selmaj K, Sorensen P S. Neutralizing antibodies to interferon beta: Expert panel report. *J. Neurol* (2007 Apr. 24) (Epub ahead of print)

Hollmann et al. (1989) Cloning by functional expression of a member of the glutamate receptor family. *Nature* 342:643-648

Heil F, Hemmi H, Hochrein H, Ampenberger F, Kirschning C, Akira S, Lipford G, Wagner H, and Bauer S. (2003). Species-specific recognition of single-stranded RNA via toll-like receptor 7 and 8. *Science*, 303, 1526-1529.

Hemmi, H., Takeuchi, O., Kawai, T., Kaisho, T., Sato, S., Sanjo, H., Matsumoto, M., Hoshino, K., Wagner, H., Takeda, K., and Akira, S. (2000). A Toll-like receptor recognizes bacterial DNA. *Nature,* 408, 740-745.

Hemmi, H., Takeuchi, O., Sato, S., Yamamoto, M., Kaisho, T., Santon H., Kawai, T., Hoshino, K., Takeda, K, and Akira, S. (2004). The roles of two ikappaB kinases in lipopolysaccharide and double stranded RNA signaling and viral infection. *J. Exp. Med.* 199, 1641-1650.

Horvath et al. (1995) A STAT protein domain that determines DNA sequence recognition suggests a novel DNA-binding domain *Genes Dev.* 9:984-994

Hwang et al. (1995) A null mutation in the gene encoding a type I interferon receptor component eliminates antiproliferative and antiviral responses to interferons alpha and beta and alters macrophage responses. *Proc Natl Acad Sci USA.* 92:11284.

Ihle, (1995) Cytokine receptor signalling. *Nature.* 377:591.

Jay et al. (1990) Primary structure of the gamma subunit of the DHP-sensitive calcium channel from skeletal muscle. *Science*

Johnson et al. (1986) *Cell* 47:545-554

Julius et al. (1988) Molecular characterization of a functional cDNA encoding the serotonin 1c receptor. *Science* 241: 558-564

Julius et al. (1990) The 5HT2 receptor defines a family of structurally distinct but functionally conserved serotonin receptors. *PNAS* 87:928-932

Kawade Y, Wantanabe Y. Neutralization of interferon by antibody: Appraisals of methods of determining and expressing the neutralization titer. *J. Interferon & Cytokine Res.* (1984) 4:571-584.

Kayano et al, (1988) Primary structure of rat brain sodium channel III deduced from the cDNA sequence. *FEBS Lett.* 228:187-194

Kobilka et al. (1987) An intronless gene encoding a potential member of the family of receptors coupled to guanine nucleotide regulatory proteins. *Nature* 329:75-79

Kobilka et al. (1987) Cloning, sequencing, and expression of the gene coding for the human platelet alpha 2-adrenergic receptor. *Science* 238:650-656

Lallemand C, Lebon P, Rizza P, Blanchard B, Tovey M G. Constitutive expression of specific interferon isotypes in peripheral blood leukocytes from normal individuals and in promonocytiv U937 cells. *J. Leuk. Biol.* (1996) 60:137-146.

Langer et al. (1996) Interferon receptors. *Biotherapy.* 8:163

Levitan et al. (1988) Structural and functional basis for GABAA receptor heterogeneity. *Nature* 335:76-79

Levy et al. (1988) Interferon-induced nuclear factors that bind a shared promoter element correlate with positive and negative control *Genes Dev.* 2:383-393

Lewis, (1995) A sensitive biological assay for interferons. *Journal of Immunological Methods* 185:9-17

Lim et al. (1993) Cloning and characterization of a bovine alpha interferon receptor. *Biochim Biophys Acta.* 1173: 314.

Lleonart et al., (1990) A novel, quantitative bioassay for type I interferon using a recombinant indicator cell line. *Biotechnology* 8:1263-1267

Lutfalla et al. (1992) The structure of the human interferon alpha/beta receptor gene. *J Biol. Chem.* 267:2802.

Lutfalla et al. (1995) Mutant U5A cells are complemented by an interferon-alpha beta receptor subunit generated by alternative processing of a new member of a cytokine receptor gene cluster. *Embo J.* 14:5100.

McCormick P L, Scott L J. Interferon-beta-1b: a review of its use in relapsing-remitting ans secondary progressive multiple sclerosis. *CNR Drugs,* (2004) 18:521-546.

McKinnon, D. (1989) Isolation of a cDNA clone coding for a putative second potassium channel indicates the existence of a gene family. *J. Biol. Chem.* 264:8230-8236

Meager A. Measurement of cytokines by bioassays: Theory and application. *Methods* (2006) 38:237-252.

Merlin et al. (1985) 125I-labelled human interferons alpha, beta and gamma: comparative receptor-binding data. *J Gen Virol.* 66:1149.

Montminy et al. (1986), Identification of a cyclic-AMP-responsive element within the rat somatostatin gene. *Proc. Natl. Acad. Sci.* 83:6682-6686

Mouchel-Vielh et al. (1992). Specific antiviral activities of the human alpha interferons are determined at the level of receptor (IFNAR) structure. *FEBS Lett.* 313:255.

Muller et al. (1994) Functional role of type I and type II interferons in antiviral defense. *Science.* 264:1918.

Namaka M, Pollitt-Smith M, Gupta A, Klowak M, Vasconcelos M, Turcotte D, Gong Y, Melanson M. *Curr. Med. Res. Opin.* (2006) 22:223-239.

Noda et al. (1986) *Nature* 320:188-192

Noronha A. Neutralizing antibodies to interferon. *Neurology*, (2007) 68(24 Suppl 4):S16-22.

Novick et al. (1994) The human interferon alpha/beta receptor: characterization and molecular cloning. *Cell.* 77:391.

Perry et al., (1999) Cloning of interferon-stimulated gene 17: The promoter and nuclear proteins that regulate transcription. *Molecular Endocrinology,* 13:1197-1206

Perry, A. K., Chow, E. K., Goodnougy, J. B., Yeh, W. C., and Cheng, G. (2004). Differential requirement for TANK-binding kinase-1 in type I interferon responses Pestka et al. (1987) Interferons and their actions. *A. Rev. Biochem.* 56:727.

Platanias et al. (1994) Tyrosine phosphorylation of the alpha and beta subunits of the type I interferon receptor. Interferon-beta selectively induces tyrosine phosphorylation of an alpha subunit-associated protein. *J. Biol. Chem.* 269:17761.

Pritchett et al. (1989) Importance of a novel GABAA receptor subunit for benzodiazepine pharmacology. *Nature* 338:582-585

Rider et al. (2003) A B cell-based sensor for rapid identification of pathogens. *Science* 301:213-215

Ritchie K J, Zhang D E. ISG15:The immunological kin of ubiquitin. *Semin. Cell Dev. Biol.* (2004) 15:237-246.

Rudick R A, Stuart W H, Calabresi P A, Confavreux C, Galetta S L, Radue E W, Lublin F D, Weinstock-Guttman B, Wynn D R, Lynn F, Panzara M A, Sandrock A W. *N. Engl. J. Med.* (2006) 354:911-923.

Russell-Harde et al. (1995) Reconstitution of a high affinity binding site for type I interferons. *J Biol. Chem.* 270:26033.

Ruth et al. (1989) Primary structure of the beta subunit of the DHP-sensitive calcium channel from skeletal muscle. *Science* 245:1115-1118

Scagnolari C, Duda P, Bagnato F, De Vito G, Alerelli A, Lavolpe V, Girand E, Durastanti V, Trojano M, Kappos L, Antonelli G. Pharmacodynamica of intrefreon beta in multiple sclerosis in patients with and without neutralizing antibodies. *J. Neurol.* (2007) 254:597-604.

Schellekens H. the immunogenicity of biopharmaceuticals. *Neurology.* (2003) 61(Suppl 5)S11-S12.

Schindler et al. (1992) Interferon-dependent tyrosine phosphorylation of a latent cytoplasmic transcription factor [see comments]. *Science.* 257:809.

Schofield et al. (1987) Sequence and functional expression of the GABA A receptor shows a ligand-gated receptor superfamily. *Nature* 328:221-227

Schumacher et al. (1994) The chicken Mx promoter contains an ISRE motif and confers interferon inducibility to a reporter gene in chick and monkey cells. *Virology* 15:203 (1):144-8

Sheng et al. (1990) The regulation and function of c-fos and other immediate early genes in the nervous system. *Neuron*

Sheppard et al *Nat. Immunol.* 2003; 4:63-68

Shivers, B. D. (1989) *Neuron* 3:327-337

Short et al. (1986) *J. Biol. Chem.* 261:9721-9726

Sorensen P S, Deisenhammer F, Duda P, Hohlfeld R, Myhr K M, Palace J, Polman C, Pozzilli C, Ross C. Guidelines for use of anti-IFN-beta antibody measurements in multiple sclerosis: report of an EFNS task force on IFN-beta antibodies in multiple sclerosis. *Eur. J. Neurol.* (2005) 12:817-827.

Steinhoff et al. (1995) Antiviral protection by vesicular stomatitis virus-specific antibodies in alpha/beta interferon receptor-deficient mice. *Journal of Virology.* 69:2153.

Steinman, R. M., and Hemmi, H. (2006). Dendritic cells: translating innate to adaptive immunity. *Curr. Top. Microbiol. Immunol.* 311, 17-58.

Stormann et al. (1990) Molecular cloning and expression of a dopamine D2 receptor from human retina. *Molec. Pharm.* 37:1-6

Tanabe et al. (1987) Primary structure of the receptor for calcium channel blockers from skeletal muscle. *Nature*

Taniguchi, (1995) Cytokine signaling through nonreceptor protein tyrosine kinases. *Science.* 268:251.

Tempel et al. (1988) Cloning of a probable potassium channel gene from mouse brain. *Nature* 332:837-839

Thoreau et al. (1991) Structural symmetry of the extracellular domain of the cytokine/growth hormone/prolactin receptor family and interferon receptors revealed by hydrophobic cluster analysis. *FEBS Lett.* 282:26.

Toh et al. (1989) Isolation and characterization of a rat liver alkaline phosphatase gene. A single gene with two promoters. *Eur. J. Biochem.* 182:231-238

Tovey M. G., Begon-Lours J, Gresser I., and Morris A. G. Marked enhancement of interferon production in 5-bromodeoxyuridine treated human lymphoblastoid cells. *Nature* (1977) 267:455-457.

Uddin et al. (1995) Interaction of the transcriptional activator Stat-2 with the type I interferon receptor. *J Biol. Chem.* 270:24627.

Uematsu, S., and Akira, S. (2007). Toll-like receptors and type I interferons. *J. Biol. Chem.* 282, 15319-15323.

Uze et al. (1990) Genetic transfer of a functional human interferon alpha receptor into mouse cells: cloning and expression of its cDNA. *Cell.* 60:225.

Uze et al. (1992) Behavior of a cloned murine interferon alpha/beta receptor expressed in homospecific or heterospecific background. *Proc Natl Acad Sci USA.* 89:4774.

Uzé et al. (1995) Alpha and beta interferons and their receptor and their friends and relations. *Journal of Interferon & Cytokine Research.* 15:3.

van den Broek et al. (1995) Antiviral defense in mice lacking both alpha/beta and gamma interferon receptors. *Journal of Virology.* 69:4792.

Vandenbroek et al. (1995) Immune defence in mice lacking type I and/or type II interferon receptors. *Immunol Rev.* 148:5.

Velazquez et al. (1995) Distinct domains of the protein tyrosine kinase tyk2 required for binding of interferon-alpha/beta and for signal transduction. *J Biol. Chem.* 270:3327.

Wada et al. (1988) Functional expression of a new pharmacological subtype of brain nicotinic acetylcholine receptor. *Science* 240:330-334

Yan et al. (1996) Molecular characterization of an alpha interferon receptor 1 subunit (IFNαR1) domain required for TYK2 binding and signal transduction. *Mol Cell Biol.* 16:2074.

Yan et al. (1996) Phosphorylated interferon-alpha receptor 1 subunit (IFNαR1) acts as a docking site for the latent form of the 113 kDa STAT2 protein. *EMBO J.* 15:1064.

Yeh et al. (1987) Ultrastructural localization of a platelet-derived growth factor/v-sis-related protein(s) in cytoplasm and nucleus of simian sarcoma virus-transformed cells. *Proc. Natl. Acad. Sci. U.S.A.* 84:2317-2321

Ymer et al. (1989) GABAA receptor beta subunit heterogeneity: functional expression of cloned cDNAs. *EMBO J.* 8:1665-1670

Yoneyama, M., Fujita, T. (2007). Function of RIG-1-like receptors in antiviral innate immunity. *J. Biol. Chem.* 282, 15315-15318.

Zlokarnik et al. (1998) Quantitation of transcription and clonal selection of single living cells with S-lactamase as reporter. *Science* 279:84-88.

What is claimed is:

1. A method for conducting a neutralization assay for the titer of antibodies in a sample, which antibodies are specific for a predetermined target molecule that activates the signal transduction activity of a cell surface protein or pattern recognition receptor, said method comprising:
preparing a serial dilution of the sample;
adding to each dilution a fixed amount of the target molecule, which amount corresponds to a predetermined unit of activity of the target molecule, and wherein the concentration of target molecule is the same in each dilution;
subjecting each dilution to a reporter gene assay to determine the amount of residual activity of the target molecule in that dilution, wherein said reporter gene assay comprises measuring the level of reporter gene product upon contact of said dilution with a cell line transformed with a construct comprising a nucleotide sequence encoding a reporter gene product, operatively linked to one or more transcription control elements that is regulated by the signal transduction activity of a cell surface protein or pattern recognition receptor in response to an extracellular signal generated by said target molecule; and
determining the dilution at which the activity of the added target molecule is reduced by a predetermined factor, x, said titer being expressed as an x-fold reduction in units of activity/ml,
wherein the cell line used in said reporter gene assay is one that has been treated with an anti-mitotic or pro-apoptotic agent so as to acquire the property that it will maintain said signal transduction activity for at least about one hour but will lose said signal transduction activity and undergo cellular death in no more than about 30 days at a temperature above freezing, thereby improving the sensitivity of the neutralization assay.

2. The method of claim 1, wherein said treated cell line, substantially immediately after being treated, has been resuspended in a solution containing a cryopreservative, frozen at about −80° C., and then thawed prior to use in said reporter gene assay.

3. The method of claim 2, wherein said cryopreservative is dimethylsulfoxide (DMSO) and said solution contains 10% DMSO.

4. The method of claim 2, wherein said cryopreservative is a combination of 2.5% dimethylsulfoxide (DMSO) and 10% glycerol.

5. The method of claim 1, wherein said anti-mitotic or pro-apoptotic agent is vinblastin.

6. The method of claim 1, wherein said anti-mitotic or pro-apoptotic agent is 5-fluorouracil.

7. The method of claim 1, wherein said anti-mitotic or pro-apoptotic agent is mitomycin C, an anti-tumor intercalating agent.

8. The method of claim 1, wherein said anti-mitotic or pro-apoptotic agent is γ-irradiation and wherein, said cell line has been irradiated with γ radiation at an intensity and for a sufficient amount of time such that the cell line maintains said signal transduction activity for at least about 1 hour but loses said signal transduction activity and undergoes cellular death in no more than about 30 days at a temperature above freezing.

9. The method of claim 1, wherein said cell surface protein is a cell surface receptor.

10. The method of claim 9, wherein said cell surface receptor is selected from the group consisting of a cytokine receptor, a growth factor receptor, a hormone receptor, a neuro receptor, a T cell receptor, an antigen receptor, and a complement receptor.

11. The method of claim 9, wherein said cell surface receptor is a Type I interferon receptor and said extracellular signal is provided by a Type I interferon as the predetermined target molecule.

12. The method of claim 11, wherein the predetermined target molecule is an interferon-α.

13. The method of claim 11, wherein the predetermined target molecule is an interferon-β.

14. The method of claim 11, wherein said one or more transcriptional control elements comprise an interferon stimulatory response element (ISRE).

15. The method of claim 14, wherein said ISRE comprises the nucleotide sequence of SEQ ID NO:5.

16. The method of claim 9, wherein said cell surface receptor is a Type II interferon receptor and said extracellular signal is provided by a Type II interferon as the predetermined target molecule.

17. The method of claim 16, wherein said one or more transcriptional control elements comprise a gamma activated sequence (GAS).

18. The method of claim 1, wherein said reporter gene product is selected from the group consisting of firefly luciferase, bacterial luciferase, jellyfish aequorin, enhanced green fluorescent protein (EGFP), chloramphenicol acetyl-transferase (CAT), dsRED, β-galactosidase, and alkaline phosphatase.

19. The method of claim 1, wherein said predetermined factor x is 10.

20. The method of claim 1, wherein the cell line is a mammalian or avian cell line.

21. The method of claim 1, wherein the cell line is a human cell line.

22. The method of claim 21, wherein the human cell line is a human promonocytic cell line.

23. The method of claim 22, wherein the human promonocytic cell line is a U937 cell line.

24. The method of claim 1, wherein said property of the cell line used in said reporter gene assay is that it will maintain said signal transduction activity for at least eight hours but will lose said signal transduction activity and undergo cellular death in no more than about 24 hours at a temperature above freezing.

25. The method of claim 1, wherein said property of the cell line used in said reporter gene assay is that it will maintain said signal transduction activity for at least eighteen hours but will lose said signal transduction activity and undergo cellular death in no more than 14 days.

* * * * *